US011458133B2

(12) United States Patent
Baltezor et al.

(10) Patent No.: US 11,458,133 B2
(45) Date of Patent: *Oct. 4, 2022

(54) METHODS FOR SOLID TUMOR TREATMENT

(71) Applicant: CRITITECH, INC., Lawrence, KS (US)

(72) Inventors: Mike Baltezor, Lawrence, KS (US);
Gere diZerega, Lawrence, KS (US);
Charles Decedue, Lawrence, KS (US);
Sam Campbell, Lawrence, KS (US);
Matt McClorey, Lawrence, KS (US)

(73) Assignee: CritiTech, Inc., Lawrence, KS (US)

( * ) Notice: Subject to any disclaimer, the term of this patent is extended or adjusted under 35 U.S.C. 154(b) by 347 days.

This patent is subject to a terminal disclaimer.

(21) Appl. No.: 16/839,737

(22) Filed: Apr. 3, 2020

(65) Prior Publication Data
US 2020/0246326 A1 Aug. 6, 2020

Related U.S. Application Data

(63) Continuation of application No. 16/512,044, filed on Jul. 15, 2019, now Pat. No. 11,033,542, which is a continuation of application No. 16/136,502, filed on Sep. 20, 2018, now Pat. No. 10,391,090, which is a continuation of application No. PCT/US2017/025718, filed on Apr. 3, 2017.

(60) Provisional application No. 62/318,014, filed on Apr. 4, 2016, provisional application No. 62/378,543, filed on Aug. 23, 2016.

(51) Int. Cl.
A61P 35/00 (2006.01)
A61K 31/475 (2006.01)
A61K 33/243 (2019.01)
A61K 9/19 (2006.01)
A61K 9/08 (2006.01)
A61K 9/10 (2006.01)
A61K 9/14 (2006.01)
A61K 31/337 (2006.01)
A61K 31/4439 (2006.01)
A61K 31/4745 (2006.01)
A61K 31/513 (2006.01)
A61K 31/555 (2006.01)
A61K 31/704 (2006.01)
A61K 31/7048 (2006.01)
A61K 31/7068 (2006.01)
A61K 47/26 (2006.01)
A61K 9/00 (2006.01)
A61K 47/10 (2017.01)

(52) U.S. Cl.
CPC .......... A61K 31/475 (2013.01); A61K 9/0019 (2013.01); A61K 9/08 (2013.01); A61K 9/10 (2013.01); A61K 9/14 (2013.01); A61K 31/337 (2013.01); A61K 31/4439 (2013.01); A61K 31/4745 (2013.01); A61K 31/513 (2013.01); A61K 31/555 (2013.01); A61K 31/704 (2013.01); A61K 31/7048 (2013.01); A61K 31/7068 (2013.01); A61K 33/243 (2019.01); A61K 47/26 (2013.01); A61P 35/00 (2018.01); A61K 47/10 (2013.01)

(58) Field of Classification Search
CPC .... A61K 31/475; A61K 35/00; A61K 33/243; A61K 9/0019; A61K 9/08; A61K 9/10; A61K 9/14; A61K 31/337; A61K 31/4439; A61K 31/4745; A61K 31/513; A61K 31/555; A61K 31/704; A61K 31/7048; A61K 31/7068; A61K 47/26; A61K 31/3317; A61P 35/00

See application file for complete search history.

(56) References Cited

U.S. PATENT DOCUMENTS

| | | | |
|---|---|---|---|
| 5,399,363 A * | 3/1995 | Liversidge | A61K 47/6929 424/490 |
| 5,626,862 A | 5/1997 | Brem et al. | |
| 5,833,891 A | 11/1998 | Subramaniam et al. | |
| 5,874,029 A | 2/1999 | Subramaniam et al. | |
| 5,874,481 A | 2/1999 | Weers et al. | |
| 5,886,026 A | 3/1999 | Hunter et al. | |
| 6,063,138 A | 5/2000 | Hanna et al. | |
| 6,113,795 A | 9/2000 | Subramaniam et al. | |
| 6,117,949 A | 9/2000 | Rathi et al. | |
| 6,221,153 B1 | 4/2001 | Castor et al. | |
| 6,348,209 B2 | 2/2002 | Placke et al. | |
| 6,419,901 B2 | 7/2002 | Placke et al. | |
| 6,562,952 B1 | 5/2003 | Rajewski et al. | |

(Continued)

FOREIGN PATENT DOCUMENTS

| | | |
|---|---|---|
| CN | 1 463 969 | 12/2003 |
| CN | 1463969 | 12/2003 |

(Continued)

OTHER PUBLICATIONS

U.S. Appl. No. 16/512,044, filed Jul. 15, 2019, Crititech, Inc.
FDA—"ABRAXANE—Prescribing Information" Oct. 1, 2012, pp. 1-19.
Gradishar, "Taxanes for the Treatment of Metastatic Breast Cancer" Breast Cancer: Basic and Clinical Research 6 (1):159-71 (Jan. 2012).

(Continued)

Primary Examiner — Jared Barsky
(74) Attorney, Agent, or Firm — McDonnell Boehnen Hulber & Berghoff LLP

(57) ABSTRACT

Disclosed herein are methods for treating solid tumors by direct injection into the tumors of chemotherapeutic particles, methods for inhibiting tumor metastasis by administering chemotherapeutic particles to a subject having a tumor, and compositions that include chemotherapeutic particles, small amounts of a polysorbate, and a carrier.

22 Claims, 4 Drawing Sheets

(56) References Cited

U.S. PATENT DOCUMENTS

| | | |
|---|---|---|
| 6,616,849 B1 | 9/2003 | Osajima et al. |
| 6,620,351 B2 | 9/2003 | Gupta et al. |
| 6,689,803 B2 | 2/2004 | Hunter |
| 6,749,868 B1 | 6/2004 | Desai et al. |
| 6,811,767 B1 | 11/2004 | Bosch et al. |
| 7,179,495 B1 | 2/2007 | Simon et al. |
| 7,208,106 B2 | 4/2007 | Shekunov et al. |
| 7,217,735 B1 | 5/2007 | Au et al. |
| 7,276,190 B2 | 10/2007 | Reverchon |
| RE40,493 E | 9/2008 | Straub et al. |
| 7,455,797 B2 | 11/2008 | Shekunov et al. |
| 7,556,798 B2 | 7/2009 | Edwards et al. |
| 7,566,436 B2 | 7/2009 | Lester et al. |
| 7,744,923 B2 | 6/2010 | Rajewski et al. |
| 7,754,777 B2 | 7/2010 | Ventosa et al. |
| 7,820,788 B2 | 10/2010 | Desai et al. |
| 7,829,598 B2 | 11/2010 | Iversen et al. |
| 7,833,444 B2 | 11/2010 | Watano |
| 8,043,631 B2 | 10/2011 | Au et al. |
| 8,138,229 B2 | 3/2012 | Desai et al. |
| 8,221,779 B2 | 7/2012 | Jonas et al. |
| 8,314,156 B2 | 11/2012 | Desai et al. |
| 8,735,394 B2 | 5/2014 | Desai et al. |
| 8,778,181 B1 | 7/2014 | Johnson et al. |
| 8,906,392 B2 | 12/2014 | Berkland et al. |
| 9,233,348 B2 | 1/2016 | Johnson et al. |
| 9,278,069 B2 | 3/2016 | Berkland et al. |
| 9,301,926 B2 | 4/2016 | Indolfi et al. |
| 9,339,554 B2 | 5/2016 | Rijcken et al. |
| 9,511,046 B2 | 12/2016 | Desai et al. |
| 9,617,338 B1 | 4/2017 | Campbell et al. |
| 9,763,946 B2 | 9/2017 | Lin |
| 9,814,685 B2 | 11/2017 | Baltezor |
| 9,895,197 B2 | 2/2018 | Poquet et al. |
| 9,918,957 B2 | 3/2018 | Baltezor |
| 10,391,090 B2 | 8/2019 | Baltezor et al. |
| 10,398,646 B2 | 9/2019 | Baltezor et al. |
| 10,507,181 B2 | 12/2019 | Baltezor et al. |
| 10,507,195 B2 | 12/2019 | Baltezor et al. |
| 10,729,673 B2 | 8/2020 | Baltezor et al. |
| 10,874,660 B2 | 12/2020 | Baltezor et al. |
| 10,894,045 B2 | 1/2021 | Baltezor et al. |
| 2001/0029264 A1 | 10/2001 | McChesney-Harris |
| 2002/0081339 A1 | 6/2002 | Menei et al. |
| 2002/0102294 A1 | 8/2002 | Bosch et al. |
| 2003/0166509 A1 | 9/2003 | Edwards et al. |
| 2003/0190284 A1 | 10/2003 | Annapragada et al. |
| 2004/0033267 A1 | 2/2004 | Merisko-Liversidge et al. |
| 2004/0092577 A1 | 5/2004 | Lerner et al. |
| 2004/0220081 A1 | 11/2004 | Kreitz et al. |
| 2005/0059613 A1 | 3/2005 | Memarzadeh et al. |
| 2005/0131057 A1 | 6/2005 | Ueno et al. |
| 2005/0238725 A1 | 10/2005 | Cunningham et al. |
| 2006/0034925 A1 | 2/2006 | Au et al. |
| 2006/0078619 A1 | 4/2006 | Woo et al. |
| 2006/0127420 A1 | 6/2006 | Chung et al. |
| 2006/0147535 A1 | 7/2006 | Muthukumaran et al. |
| 2006/0188566 A1* | 8/2006 | Liversidge ........... A61K 31/337 424/464 |
| 2008/0063699 A1 | 3/2008 | Teifel et al. |
| 2008/0089944 A1 | 4/2008 | Rajewski et al. |
| 2008/0160095 A1 | 7/2008 | Desai et al. |
| 2009/0215882 A1 | 8/2009 | Bouzada et al. |
| 2010/0197944 A1 | 8/2010 | Palle et al. |
| 2011/0223203 A1 | 9/2011 | Berkland et al. |
| 2011/0293672 A1 | 12/2011 | Lewis et al. |
| 2012/0087984 A1 | 4/2012 | Liversidge et al. |
| 2012/0177910 A1 | 7/2012 | Weber et al. |
| 2012/0237768 A1 | 9/2012 | Hirokawa et al. |
| 2012/0321698 A1 | 12/2012 | Narain et al. |
| 2014/0038931 A1 | 2/2014 | Hirokawa et al. |
| 2014/0079782 A1 | 3/2014 | York et al. |
| 2014/0154269 A1 | 6/2014 | Tour et al. |
| 2014/0199244 A1 | 7/2014 | Rijcken et al. |
| 2014/0243364 A1 | 8/2014 | Agisim et al. |
| 2014/0294967 A1 | 10/2014 | Borbely et al. |
| 2015/0037252 A1 | 2/2015 | Hawkett et al. |
| 2015/0118311 A1 | 4/2015 | Zhou et al. |
| 2015/0342872 A1 | 12/2015 | Williamson et al. |
| 2015/0375153 A1 | 12/2015 | Johnson et al. |
| 2016/0257752 A1 | 9/2016 | Kim et al. |
| 2016/0263232 A1 | 9/2016 | Amighi et al. |
| 2016/0339090 A1 | 11/2016 | Hacohen et al. |
| 2016/0354336 A1 | 12/2016 | Baltezor et al. |
| 2016/0362658 A1 | 12/2016 | Leen et al. |
| 2016/0374953 A1 | 12/2016 | Baltezor |
| 2017/0119881 A1 | 5/2017 | Saha et al. |
| 2017/0165369 A1 | 6/2017 | Bender |
| 2018/0169058 A1 | 6/2018 | Baltezor |
| 2018/0177739 A1 | 6/2018 | Johnson et al. |
| 2018/0306748 A1 | 10/2018 | Seuthe |
| 2018/0360748 A1 | 12/2018 | Baltezor et al. |
| 2019/0127803 A1 | 5/2019 | Hacohen et al. |
| 2019/0151478 A1 | 5/2019 | Valton et al. |
| 2020/0246326 A1 | 8/2020 | Baltezor et al. |
| 2020/0405684 A1 | 12/2020 | Baltezor et al. |
| 2021/0000786 A1 | 1/2021 | Baltezor et al. |

FOREIGN PATENT DOCUMENTS

| | | |
|---|---|---|
| CN | 1923189 | 3/2007 |
| CN | 101129338 | 2/2008 |
| CN | 101336899 A | 1/2009 |
| CN | 101 829 061 | 9/2010 |
| CN | 101829061 | 9/2010 |
| CN | 102488682 | 6/2012 |
| CN | 107281502 | 10/2017 |
| EP | 3181123 | 6/2017 |
| JP | H11279052 | 10/1999 |
| PT | 104693 | 1/2011 |
| TW | 201408304 | 3/2014 |
| WO | 2000/57852 A2 | 10/2000 |
| WO | 2000/072827 | 12/2000 |
| WO | 2001/36007 A2 | 5/2001 |
| WO | WO 02/087563 | 11/2002 |
| WO | 2003/032906 | 4/2003 |
| WO | WO 03/030941 | 4/2003 |
| WO | WO 03/090715 | 11/2003 |
| WO | WO 03/090722 | 11/2003 |
| WO | WO 2004/009076 | 1/2004 |
| WO | WO 2004/089291 | 10/2004 |
| WO | WO 2005/025542 | 3/2005 |
| WO | 2006/068890 A2 | 6/2006 |
| WO | WO 2006/099385 | 9/2006 |
| WO | 2006/103112 A2 | 10/2006 |
| WO | 2007/027941 A2 | 3/2007 |
| WO | 2007/104549 A2 | 9/2007 |
| WO | WO 2008/137148 | 11/2008 |
| WO | 2009/111271 A1 | 9/2009 |
| WO | WO 2011/153009 | 12/2011 |
| WO | 2012/051426 | 4/2012 |
| WO | WO 2015/103005 | 7/2015 |
| WO | WO 2015/187194 | 12/2015 |
| WO | WO 2016/197091 | 12/2016 |
| WO | WO 2017/049083 | 3/2017 |
| WO | WO 2017/053920 | 3/2017 |
| WO | WO 2017/127729 | 7/2017 |
| WO | WO 2017/176628 | 10/2017 |
| WO | WO 2018/045239 | 3/2018 |
| WO | WO 2018/170196 | 9/2018 |
| WO | WO 2018/170207 | 9/2018 |
| WO | WO 2018/170210 | 9/2018 |
| WO | WO 2018/227037 | 12/2018 |
| WO | WO 2018/231908 | 12/2018 |

OTHER PUBLICATIONS

Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice" Cancer Research 61:3689-97 (May 2001).

(56) References Cited

OTHER PUBLICATIONS

Manthey et al., "Taxol increases steady-state levels of lipopolysaccharide-inducible genes and protein-tyrosine phospohorylation in murine macrophages" The Journal of Immunology 149(7):2459-2465 (Oct. 1992).
Monette et al., "Chitosan thermogels for local expansion and delivery of tumor-specific T lymphocytes towards enhanced cancer immunotherapies" Biomaterials 75:237-49 (Jan. 2016).
Zhong et al., "Low-dose paclitaxel prior to intrtumoral dendtritic cell vaccine modulates intratumoral cytokine network and lung cancer growth" Clinical Cancer Research 13(18):5455-62 (Sep. 2007).
U.S. Appl. No. 17/023,098, filed Sep. 16, 2020, Crititech, Inc.
U.S. Appl. No. 17/023,635, filed Sep. 17, 2020, Crititech, Inc.
Maude et al. "Chimeric Antigen Receptor T Cells for Sustained Remissions in Leukemia," N Engl J Med 371;16 Oct. 16, 2014.
Mayo Clinic—Patient care and health information regarding cycstic fibrosis, accessed online Sep. 10, 2018, pp. 1-8.
Mcgrath "Management of incidental pancreatic cysts: which guidelines?" Endoscopy International Open 2017; 05: E209-E211.
Mckiernan et al, "Phase I trail of intravesical docetaxel in the management of superficial bladder cancer refractory to standard intravesical therapy" Journal of Clinical Oncology, vol. 24, No. 19, 2006.
Mckiernan et. al. "Phase II Trial of intravesical nanoparticle albumin bound paclitaxel for the treatment of nonmuscle invasive urothelial carcinoma of the bladder after bacillus Calmette-guerin treatment failure" The Jounral of Urology, vol. 192, 1633-1638, 2014.
Michels et. al. "Paclitaxel promotes differentiation of myeloid-derived suppressor cells into dendritic cells in vitro in a TLR4-independent manner". J Immunotoxicol. 2012; 9:292-300.
Mills et al. "Possible Drug-Associated Pancreatitis after Paclitaxel-Cremophor Administration," Pharmacotherapy: The Journal of Human Pharmacology and Drug Therapy, vol. 20, Issue 1, Jan. 2000, pp. 95-97.
Mirvish et al. "Dendritic Cell Vaccines in Cancer: Obstacles to Overcome," Chapter 21, Dendritic Cells in Cancer, Shurin et al. (eds.) Springer Science + Business Media, LLC 2009.
Moyer et al. "Is alcohol required for the effective pancreatic cyst ablation? The prospective randomized CHARM trial pilot study," Endoscopy International Open, 2016; 04: E603-E607.
Muller et al. "Challenges and solutions for the delivery of biotech drugs—a review of drug nanocrystal technology and lipid nanoparticles," Journal of Biotechnology 113 (2004) 151-170.
Nars et. al. "Immunomodulatory effects of low dose chemotherapy and perspectives of its combination with immunotherapy." International journal of cancer 132.11 (2013): 2471-2478.
Necchi et al., "918TiP: Pembrolizumab and nanoparticle albumin bound paclitaxel (nabpaclitaxel) for metastatic urothelial carcinoma (UC) after chemotherapy failure: the open-label. single-arm. phase 2 PEANUT study." Annals of Oncology 42nd ESMO Congress, ESMO 2017 Madrid Spain, 28(Supplement5):v325-v326 (Sep. 2017).
NSST Technical Report, 1503-1, URL: https://www.nsst.nssmc.com/techrepo/zairyo_pdf/HRM-1503.pdf.
Nayyar et al. "Overcoming Resistance to Natural Keller Cell Based Immunotherapies for Solid Tumors," Frontiers in Oncology, vol. 9, Article 51, Feb. 11, 2019.
O'shaughnessy, et al. "Systemic Antitumor Immunity by PD-1/PD-L1 Inhibition is Potentiated by Vascular-Targeted Photodynamic Therapy of Primary Tumors," Clinical Cancer Research, 24(3): 592-599, Sep. 2017.
Oh et al. "Endoscopic Ultrasonography-Guided Ethanol Lavage with Paclitaxel Injection Treats Patients with Pancreatic Cysts," Gastroenterology 2011;140:172-179.
Pazdur, et al., (The toxoids: paclitaxel (Taxol) and docetaxel (Taxotere, Cancer treatment reviews, 19(4): 351-386 (1993).
Pettitt et al. "CAR-T Cells: A Systematic Review and Mixed Methods Analysis of the Clinical Trial Landscape," Molecular Therapy, vol. 26, No. 2, Feb. 2018.

Pitman et al. "Pancreatic Cysts Preoperative Diagnosis and Clinical Management," Cancer Cytopathology, Feb. 25, 2010, pp. 1-13, published online Dec. 30, 2009.
Pretto et al. "Preclinical evaluation of IL2-based immunocytokines supports their use in combination with dacarbazine, paclitaxel and TNF-based immunotherapy." Cancer Immunology, Immunotherapy 63.9 (2014): 901-910.
Provenge® Presribing Information, Rev. Jul. 2017, 2 pages.
Raju et. al. "Review of checkpoint immunotherapy for the management of non-small cell lung cancer" Immuno Targets and Therapy, 2018;7 63-75.
Rampersaud et. al. "Commentary on Hyperthermia as a treatment for bladder cancer" Oncology 2010 24(12); 1155-1160.
Saltus "Enhancing Immunotherapy: The Race to Make Cold Tumors Hot" published online on Apr. 27, 2018 at https://www.dana-farber.org/newsroom/publications/paths-of-progress-2018/enhancing-immunotherapy/.
Sarr et al. "Cystic Neoplasms of the Pancreas: Benign to Malignant Epithelial Neoplasms," Surgical Clinics of North America, vol. 81, Issue 3, Jun. 1, 2001, pp. 497-509.
Sautes-Fridman et. al. "Tertiary Lymphoid Structures in Cancers: Prognostic Value, Regulation, and Manipulation for Therapeutic Intervention" Front. Immunol. 7;407, 2016.
Schumacher et. al. "Neoantigens in cancer immunotherapy" Science vol. 348, Issue 6230, Apr. 3, 2015.
Sevko Antitumor effect of paclitaxel is mediated by inhibition of myeloid-derived suppressor cells and chronic inflammation in the spontaneous melanoma model. J. Immunol. 190, 2464 2471 (2013).
Sevko et al. Application of paclitaxel in low non-cytotoxic doses supports vaccination with melanoma antigens in normal mice. J Immunotoxicol. Jul.-Sep. 2012;9(3):275-81.
Shi et. al. "PD-1 Blockade Boosts Radiofrequency Ablation-Elicited Adaptive Immune Responses against Tumor" Clin. Cancer Res; 22(5); 1179-84, 2016.
Shurin et al. "Cancer Therapy and Dendritic Cell Immunomodulation," Chapter 14, Dendritic Cells in Cancer, Shurin et al. (eds.) Springer Science + Business Media, LLC 2009.
Slovin "Chemotherapy and immunotherapy combination in advanced prostate cancer." Clin Adv Hematol Oncol 10.2 (2012): 90-100.
Soliman "nab-Paclitaxel as a potential partner with checkpoint inhibitors in solid tumors" Onco Targets and Therapy 10:101-112 (Dec. 2016).
Stark et al. "Pancreatic Cyst Disease A Review," JAMA May 3, 2016 vol. 315, No. 17.
Tanaka et al. "Clinical aspects of intraductal papillary mucinous neoplasm of the pancreas," J Gastroenterol 2005; 40:669-675.
Tanaka et al. "International consensus guidelines 2012 for the management of IPMN and MCN of the pancreas," Pacreatology 12 (2012) 183-197.
Tanaka "Current best practice and controversies in the follow up of patients with asymptomatic branch duct IPMN of the pancreas," HPB 2016, 18, 709-711.
Vanneman et. al. Combining immunotherapy and targeted therapies in cancer treatment. Nat. Rev. Cancer 12, 237-251, 2012.
Vaz-Luis et. al. "Survival Benefit Needed to Undergo Chemotherapy: Patient and Physician Preferences" Cancer Aug. 1, 2017, 2821-2828, published online Mar. 21, 2017 in Wiley Online Library (wileyonlinelibrary.com).
Worley et. al. "Docetaxel accumulates in lymphatic circulation following subcutaneous delivery compared to intravenous delivery in Rats" Anticancer Research 36; 5071-5078 (2016).
Wu et al. "Physical and chemical stability of drug nanoparticles," Advanced Drug Delivery Reviews 63 (2011) 456-469.
Wysham et al. "Adding bevacizumab to single agent chemotherapy for the treatment of platinum-resistant recurrent ovarian cancer: A cost effectiveness analysis of the Aurelia trial" Gynecologic Oncology 145 (2017) 340-345.
Yu et al. "Tumor-immune profiling of murine syngeneic tumor models as a framework to guide mechanistic studies and predict therapy response in distinct tumor microenvironments," PLOS ONE https://doi.org/10.1371/journal. pone.0206223 Nov. 2, 2018.

(56) References Cited

OTHER PUBLICATIONS

Ze et al., "Paclitaxel Gelatin Nanoparticles for Intravesical Bladder Cancer Therapy," Journal of Urology, vol. 185, No. 4, Apr. 2011, pp. 1478-1483.
Zhang et. al. MTDH/AEG-1 based DNA vaccine suppresses metastasis and enhances chemosensitivity to paclitaxel in pelvic lymph node metastasis Biomedicine & Pharmacotherapy 70 (2015) 217-226.
Zhang et al. "Endoscopic ultrasound-guided ethanol ablation therapy for tumors," World J Gastroenterol Jun. 14, 2013; 19(22): 3397-3403.
Zhao et. al. "New Avenues for Nanoparticle-Related Therapies" Nanoscale Research Letters (2018) 13;136.
Zheng et. al. "Chemotherapy-induced immunomodulation in non-small-cell lung cancer: a rationale for combination chemoimmunotherapy" Immunotherapy (2017) 9(11), 913-927.
Zitvogel et. al. "Mechanism of action of conventional and targeted anticancer therapies: reinstating immunosurveillance." Immunity 39.1 (2013): 74-88.
U.S. Appl. No. 16/383,023, filed Jan. 4, 2019, Crititech, Inc.
U.S. Appl. No. 16/239,531, filed Jan. 4, 2019, Crititech, Inc.
U.S. Appl. No. 16/239,530, filed Jan. 4, 2019, Crititech, Inc.
U.S. Appl. No. 16/239,533, filed Jan. 4, 2019, Crititech, Inc.
U.S. Appl. No. 16/239,527, filed Jan. 4, 2019, Crititech, Inc.
U.S. Appl. No. 16/239,529, filed Jan. 4, 2019, Crititech, Inc.
U.S. Appl. No. 15/895,197, filed Feb. 13, 2018, Crititech, Inc.
U.S. Appl. No. 15/499,397, filed Apr. 27, 2017, Crititech, Inc.
U.S. Appl. No. 15/261,108, filed Sep. 9, 2016, Crititech, Inc.
U.S. Appl. No. 15/174,505, filed Jun. 6, 2016, Crititech, Inc.
U.S. Appl. No. 16/136,502, filed Sep. 20, 2018, Crititech, Inc.
U.S. Appl. No. 16/382,446, filed Apr. 12, 2019, Crititech, Inc.
U.S. Appl. No. 16/007,095, filed Jun. 13, 2018, Crititech, Inc.
U.S. Appl. No. 16/444,299, filed Jun. 18, 2019, Crititech, Inc.
Johnston, et al., "Nanotax Injectable Nanocystal Paclitaxel for Ovarian and other Intraperitoneal Cancers," Datasheet, Sep. 2013.
Bouquet, et al., "Drug Delivery of paclitaxel for an intraperitoneal chemotherapy," Thesis, 2009.
Merisko-Liversidge, et al., "Formulation and Antitumor Activity Evaluation of Nanocrystalline Suspensions of Poorly Soluble Anticancer Drugs," Pharmaceutical Research, 13(2): 272-278, 1996.
Sharma, et al. "Development of Stabilized Paclitaxel nanocrystals: In vitro and in vivo efficacy studies," European Jounral of Pharmaceuticals Science, 69: 51-60, Jan. 2015.
Pankaj, et al., Nanosized Paclitaxel Particles from Supercritical Carbon Dioxide Processing and Their Biological Evaluation, Langmuir, 23(5): 2674-2679, Feb. 2007.
Della Porta and Reverchon, "Engineering Powder Properties by supercritical fluid for optimum Drug Delivery, Part One Supercritical Antisolvent Precipitation,"BioProcessTechnical, Feb. 2005, 48-52.
Della Porta and Reverchon, Engineering Powder Properties by supercritical fluid for optimum Drug Delivery, Part Two Supercritical Assisted Atomization, BioProcess Technical, Mar. 2005, 54-60.
Charoenchaitrakool, et al., "Micronization by Rapid Expansion of Supercritical Solutions to Enhance the Dissolution Rates of Poorly Water-Soluble Pharmaceuticals," Ind Eng Chem Res, 2000, 39: 4794-4802.
Werth, et al., "Agglomeration of Charged Nanopowders in Suspensions," Phys Rev E Stat Nonlin Soft Matter Phys. Feb. 2006;73(2 Pt 1 ):021402. Epub Feb. 10, 2006.
Rasenack, et al., Micronization of Anti-Inflammatory Drugs for Pulmonary Delivery by a Controlled Crystallization Process, J Pharm Sci, 92:35-44, 2003_.
Castellanos, "The relationship between attractive interparticles forces and bulk behaviors in dry and uncharged fine powders," Advances in Physics, 54(4): 263-376, 2005.
Snavely, et al., "Micronization of insulin from halogenated alcohol solution using supercritical carbon dioxide as an antisolvent," J Pharm Sci, 91:2026-2039, 2002.
Vemavarapu, Particle formation by rapid expansion of supercritical solutions, Dissertation 2002.

Podczeck, "The Influence of Particle Size Distribution and Surface Roughness of Carrier Particles on the in vitro Properties of Dry Powder Inhalations," Aerosol Science and Technology, 31(4): 301-321, 1999.
Young Characterisation of particle-particles interactions using the atomic force microscope, Dissertation, 2002.
Barura, et al "Challenges associated with penetration of nanoparticles across cell and tissue barriers: A review of current status and future prospects," Nano Today, 9: 223-243, 2014.
Carbone, et al "Non-Small Cell Lung Cancer: Role of the Immune System and Potential for Immunotherapy," J Thorac Oncol, 10(7): 974-984, 2015.
Desai, et al. "Pulmonary delivery of a novel, cremophor-free, protein-based nanoparticle preparation of paclitaxel," Proceedings of the American Association for Cancer Research, 44: 731-732, Abstract 2003.
Hiraoka et al. "Concurrent infiltration by COB+ T cells and CD4+ T cells is a favourable prognostic factor in non-small-cell lung carcinoma," British Journal of Cancer, 94: 275-280, 2006.
Hershey, et al. "Inhalation Chemotherapy for Macroscopic Primary or Metastatic Lung Tumors: Proof of Principle Using Dogs with Spontaneously Occurring Tumors as a Model," Clinical Cancer Research, 5:2653-2659, 1999.
Hohenforst-Schmidt "Intratumoral chemotherapy for lung cancer: re-challenge current targeted therapies," Drug Design, Development and Therapy, 571-583, 2013.
Koshkina, et al. "Paclitaxel Liposome Aerosol Treatment Induces Inhibition of Pulmonary Metastases in Murine Renal Carcinoma Model," Clinical Cancer Research, 7: 3258-3262, Mar. 2001.
Koshkina, et al. "Improved respiratory delivery of the anticancer drugs, camptothecin and paclitaxel, with 5% C02-enriched air: pharmacokinetic studies," Cancer Chemother Pharmacol, 47:451-456, Oct. 2001.
Koshkina, et al. "Cyclosporin A Aerosol Improves the Anticancer Effect of Paclitaxel Aerosol in Mice," Journal of Aerosol Medicine, 17(1): 7-14, 2004.
Kulkarni, et al. "The Use of Systemic Treatment in the Maintenance of Patients with Non-Small Cell Lung Cancer: A Systematic Review," Journal of Thoracic Oncology, 11(7): 989-1002, 2016.
Liu et al. "Paclitaxel Nanocrystals for Overcoming Multidrug Resistance in Cancer," Mol. Pharm. 7(3): 863-869, 2010.
Mallow et al. Broncho-Adventitial Delivery of Paclitaxel to Extend Airway Patency in Malignant airway Obstruction (broadway trial), Advances in Thoracic Oncologic Diagnostics, Abstract May 2017.
Polo et al. "Maintenance strategies in stage IV non-small-cell lung cancer (NSCLC): in which patients, with which drugs?" Annals of Oncology 25: 1283-1293, Dec. 2013.
Wakabayashi et al. "CD4+ T cells in cancer stroma, not COB+ T cells in cancer cell nests, are associated with favorable prognosis in human non-small cell lung cancers," Cancer Sci, 94( 11 ): 1003-1009, Nov. 2003.
King et al. "Efficacy and safety of albumin-bound paclitaxel in treating recurrent advanced non-small-cell lung cancer," Chinese Journal of Cancer Research, 25(2):200-205, 2013.
Zarogoulidis et al. "Inhaled chemotherapy in lung cancer: future concept of nanomedicine," International Journal of Nanomedicine, 7: 1551-1572, Mar. 2012.
Zhou "Atomized paclitaxel liposome inhalation treatment of bleomycin-induced pulmonary fibrosis in rats," Genetics and Molecular Research, 15(2): 1-11, 2016.
clinical trials.gov "OGX-011 and Docetaxel in Treating Patients with Metastatic or Locally Recurrent Solid Tumors" May 10, 2007.
De Smet et al., "Development of a Nanocrystalline Paclitaxel Formulation for Hipec Treatment" Pharm. Research 29:2398-2406 (2012).
Liu et al, "Enabling Anticancer Therapeutics by Nanoparticle Carriers: The Delivery of Paclitaxel," Int J. Mol. Sci., 12:4395-4413, 2011.
Weiss et al. "A phase Ib study of pembrolizumab plus chemotherapy in patients with advanced cancer (PembroPlus)." British Journal of Cancer (2017).
Anastasiadis et. al. "Best practice in the treatment of nonmuscle invasive bladder cancer" Ther Adv Urol (2012) 4(1) 13-32.

(56) References Cited

OTHER PUBLICATIONS

Asmawi et al. "Excipient selection and aerodynamic characterization of nebulized lipid-based nanoemulsion loaded with docetaxel for lung cancer treatment", Drug Delivery and Translational Research, vol. 9, No. 2, Apr. 2018, pp. 543-554.
Atar et al. "EUS Guided Injection of Albumin Bound Paclitaxel Into Mucinous Pancreatic Cysts," Gastrointestinal Endoscopy, vol. 81, No. 5S : 2015.
Bharadwaj et al. "Topical delivery of paclitaxel for treatment of skin cancer," Drug Development and Industrial Pharmacy, vol. 42, No. 9, Mar. 2016, pp. 1482-1494.
Bilusic et. al. "Immunotherapy of Prostate Cancer: Facts and Hopes", Clin Cancer Res; 23(22); 6764-70, 2017.
Bracci et al. "Immune-Based mechanisms of cytotoxic chemotherapy: implications for the design of novel and rationale-Based combined treatments against cancer." Cell Death and Differentiation, vol. 21, No. 1, 2013, pp. 15-25., doi:10.1038/cdd.2013.67.
Buda et. al. "Randomised controlled trial comparing single agent paclitaxel vs epidoxorubicin plus paclitaxel in patients with advanced ovarian cancer in early progression after platinum-based chemotherapy", British Journal of Cancer (2004) 90, 2112-2117.
Butterfield "Cancer vaccines" BMJ. 2015; 350; h988.
Cao et. al. "Tumor associated macrophages and angiogenesis dual-recognizable nanoparticles for enhanced cancer chemotherapy" Nanomedicine: Nanotechnology, Biology, and Medicine 14 (2018) 651-659.
Celegene "What is the optimal chemotherapy partner for immune checkpoint inhibitor drugs?" Presentation Mar. 16, 2017 by Eric Raymond at Mediterranean Institute for Life Sciences, Republic of Croatia, 73 pages.
Chan et. al. "The immunological effects of taxanes". Cancer Immunol. Immunother. Jul. 2000;49(4-5):181-5.
Chen et. al. "Chemoimmunotherapy: reengineering tumor immunity". Cancer Immunol. Immunother. 62, 203-216, 2013.
Choi et. al. "Long-term outcomes after endoscopic ultrasound-guided ablation of pancreatic cysts," Endoscopy, 2017; 49: 866-873.
clinicals.gov "A study of Pembrolizumab (MK-3475) in combination with chemotherapy or immunotherapy in participants with lung cancer" Jan. 16, 2014.
Colbeck et. al. "Tertiary Lymphoid Structures in Cancer: Drivers of Antitumor Immunity, Immunosuppression, or Bystander Sentinels in Disease?" Front Immunol, 8, 1830. doi:10.3389/fimmu.2017.01830.
Crown et al., "Docetaxel and Paclitaxel in the treatment of breast cancer: A review of clinical experience," The Oncologist (2004) vol. 9(2), pp. 24-32.
Deng et al. "Understanding the Structure and Stability of Paclitaxel nanocrystals," Int J Pharm May 10, 2010, 390(2): 242-249.
Dewitt et al. "Alteration in cyst fluid genetics following endoscopic ultrasound-guided pancreatic cyst ablation with ethanol and paclitaxel," Endoscopy 2014; 46(06): 457-464.
Dewitt "Pancreatic cyst ablation: why are we not doing more of these procedures?" Endoscopy, 2017; 49: 839-841.
Diaz et al. "Concomitant combination of active immunotherapy and carboplatin-or paclitaxel-based chemotherapy improves anti-tumor response." Cancer Immunology, Immunotherapy 62.3 (2013): 455-469.
Eisenhauer et. al. "New response evaluation criteria in solid tumours: Revised RECIST guideline (version 1.1)" European Journal of Cancer 45 (2009) 228-247.
Farrell "Prevalence, Diagnosis and Management of Pancreatic Cystic Neoplasms: Current Status and Future Direction," Gut and Liver, vol. 9, No. 5, Sep. 2015, pp. 571-589.
Farrell et al. "Pancreatic Cystic Neoplasms: Management and Unanswered Questions," Gastroenterology 2013;144:1303-1315.
Ferenbach et. al. "Macrophages and dendritic cells: what is the difference?" Kidney International (2008) 74.
Finkelstein et. al. "Serial assessment of lymphocytes and apoptosis in the prostate during coordinated intraprostatic dendritic cell injection and radiotherapy" Immunotherapy (2012) 4 (4), 373-382.
Forde et. al. "Neoadjuvant PD-1 Blockade in Resectable Lung Cancer" N Engl J Med 2018; 378;1976-86.
Gajewski "Fast Forward—Neoadjuvant Cancer Immunotherapy" N Engl J Med 378;21 May 24, 2018, 2034-35.
Galluzzi et. al. The secret ally: immunostimulation by anticancer drugs. Nat. Rev. Drug Discov. 11, 215-233, 2012.
Garnett et. al. "Combination of docetaxel and recombinant vaccine enhances T-cell responses and antitumor activity: effects of docetaxel on immune enhancement." Clinical Cancer Research 14.11 (2008): 3536-3544.
Ghosh et al. "Nanosuspensions for improving the bioavailability of a poorly soluble drug and screening of stabilizing agents to inhibit crystal growth," International Journal of Pharmaceutics 409 (2011) 260-268.
Goel, et al., "Exploring targeted pulmonary delivery for treatment of lung cancer," IntJ Pharm Investig (2013) 3(1):8-14.
Gomez et al. "EUS-guided ethanol lavage does not reliably ablate pancreatic cystic neoplasms," Gastrointestinal Endoscopy vol. 83, No. 5 : 2016.
Govindan et al. "Phase III trial of ipilimumab combined with paclitaxel and carboplatin in advanced squamous non-small-cell lung cancer." Journal of Clinical Oncology (2017): JCO—2016.
Gruden et al., "Antitumoral effect and reduced systemic toxicity in mice after intra-tumoral injection of an in vivo solidifying calcium sulfate formulation with docetaxel", European Journal of Pharmaceutics and Biopharmaceutics, 114 (2017); 186-193.
Grünwald et al. "The role of nephrectomy in metastatic renal cell carcinoma" Nature Reviews Nephrology 14(10):601-602 (Oct. 2018).
Gulley et. al. "Phase I study of intraprostatic vaccine administration in men with locally recurrent or progressive prostate cancer". Cancer Immunol Immunother, 2013;62,1521-1531.
"Inman, ""Atezolizumab/Nab-Paclitaxel Combo Shows High Response Rates in TNBC"". Internet Citation. Dec. 10, 2015. Retrieved from the Internet:URL:http://www.onclive.comjconference-coverage/sabcs-2015/atezolizumab-nab-paclitaxel-combo-shows-high-response-rates-in-tnbc [retrieved Oct. 20, 2017]."
Janeway et al. "Using the immune response to attack tumors," Immunobiology: The Immune System in Health and Disease, 5th ed, New York: Garland Science; 2001.
Javeed et. al. Paclitaxel and immune system. Eur J Pharm Sci. Nov. 5, 2009;38(4):283-90.
Kalos et al. "T Cells with Chimeric Antigen Receptors Have Potent Antitumor Effects and Can Establish Memory in Patients with Advanced Leukemia," Sci Transl Med. Aug. 10, 2011; 3(95) 95ra73.
Kirtane, et al., "EUS for pancreatuc cycstic neoplasms: The roadmap to the future us much more than just a few shades of gray," Asian Pacific Jounral of Tropical Medicine (2016) 9(12), pp. 1218-1221.
Kodumudi et. al. A novel chemoimmunomodulating property of docetaxel: suppression of myeloid-derived suppressor cells in tumor bearers. Clin. Cancer Res. 16, 4583-4594, 2010.
Le Visage, et al., "Efficacy of PaclitaxelReleased From Bio-Adhesive Polymer Microspheres on Model Superficial Bladder Cancer," Journal of Urol, vol. 171, No. 3, Mar. 2004, pp. 1324-1329.
Lee et al, "Macrophage-Based Cell Therapies: The Long and Winding Road," J Control Release. Oct. 28, 2016; 240: 527-540.
Liu et. al. Pre-treatment with chemotherapy can enhance the antigenicity and immunogenicity of tumours by promoting adaptive immune responses. Br. J. Cancer 102, 115-123, 2010.
Lu et al. "Mucoadhesive polyacrylamide nanogel as a potential hydrophobic drug carrier for intravesical bladder cancer therapy", European Journal of Pharmaceutical Sciences, vol. 72, Mar. 2015, pp. 57-68.
Lu et. al. "Paclitaxel-loaded gelatin nanoparticle for intravesical bladder cancer therapy" Clinical Cancer Research vol. 10, Issue 22, Nov. 2004.
Lu et. al. "Paclitaxel Gelatin nanoparticles for Intravesical Bladder Cancer Therapy" The Journal of Urology vol. 185, 1478-1483, Apr. 2011.
Lu et al. "Combined PD-1 blockade and GITR triggering induce a potent antitumor immunity in murine cancer models and synergizes with chemotherapeutic drugs." Journal of translational medicine 12.1 (2014): 36.

(56) References Cited

OTHER PUBLICATIONS

Marabelle, et al. "Starting the Fight in the Tumor: expert Recommendation for the Development of Human Intratumoral Immunotherapy (HIT-IT)" Published by Oxford University Press on behalf of the European Society for Medical Oncology. 2018.
Carson et al. "Cellular immunity in breast cancer patients completing taxane treatment" Clinical Cancer Research 10:3401-09 (May 2004).
Ma et al., "Effective antitumor activity of paclitaxel-loaded poly (epsiloncaprolactone)/pluronic F68 nanoparticles after intratumoral delivery into the murine breast cancer model," Anti-Cancer Drugs, 21(3):261-69 (2010).
Roby et al., "Syngeneic mouse model of epithelial ovarian cancer: effects of nanoparticulate paclitaxel, Nanotax®," Advances in Experimental Medicine and Biology, 622:169-81 (2008).
Saloustros et al., (Expert Opin. Pharmacother. (2008) 9(15):2603-2616) (Year: 2008).
Socinski et al. (Current Oncology, vol. 21, No. 5, Oct. 2014, pp. e691-703 (Year: 2014).
Zheng et al., "Enhanced antitumor efficiency of docetaxel-loaded nanoparticles in a human ovarian xenograft model with lower systemic toxicities by intratumoral delivery," Oncology Reports, 23(3):717-24 (2010).
Al-Ghananeem et al. "Intratumoral Delivery of Paclitaxel in Solid Tumor from Biodegradable Hyaluronan Nanoparticle Formulations," AAPS PharmSciTech, vol. 10, No. 2, Jun. 2009.
Amiji et al. "Intratumoral Administration of Paclitaxel in an In Situ Gelling Poloxamer 407 Formulation," Pharmaceutical Development and Technology, 7(2), 129-202 (2002).
Arnone et al. "Commentary: Current status of intratumoral therapy for glioblastoma," J Neurol Neuromed (2016) 1(6):27-31.
Axiak-Bechtel et al. "Nanoparticulate paclitaxel demonstrates antitumor activity in PC3 and Ace-1 aggressive prostate cancer cell lines," Invest New Drugs. 2013;31:1609-1615.
Desai et al. "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel," Clin Cancer Res 2006;12(4).
Desai et al. "Improved effectiveness of nanoparticle albumin-bound (nab) paclitaxel versus polysorbate-based docetaxel in multiple xenografts as a function of HER2 and SPARC status," Anti-Cancer Drugs 2008, 19:899-909.
Elstad et al. "OncoGel (ReGel/paclitaxel)—Clinical applications for a novel paclitaxel delivery system," Advanced Drug Delivery Reviews 61 (2009) 785-794.
Engels et al. "Alternative drug formulations of docetaxel: a review," Anti-Cancer Drugs 2007 18:95-103.
Feng et al. "A critical review of lipid-based nanoparticles for taxane delivery," Cancer Letters 334 (2013) 157-175.
Goldberg et al. "Intratumoral cancer chemotherapy and immunotherapy: opportunities for nonsystemic preoperative drug delivery," JPP 2002, 54: 159-180.
Gu et al. "Nanoformulation of paclitaxel to enhance cancer therapy," Journal of Biomaterials Applications 28(2) 198-307 2012.
Hosein et al. "A phase II trial of nab-Paclitaxel as second-line therapy in patients with advanced pancreatic cancer. Am J Clin Oncol," Apr. 1, 2013; 36(2):151-6.
Hussain et al. "Long-term follow-up of a prospective trial of trimodality therapy of weekly paclitaxel, radiation, and androgen deprivation in high-risk prostate cancer with or without prior prostatectomy," Int J Radiation Oncology Biol Phys. 2012;82(1):167-174.
Indolfi et al. "A tunable delivery platform to provide local chemotherapy for pancreatic ductal adenocarcinoma. Biomaterials," 2016;93:71-82.
Jackson et al. "The Suppression of Human Prostate Tumor Growth in Mice by the Intratumoral Injection of a Slow-Release Polymeric Paste Formulation of Paclitaxel," Cancer Research 60, 4146-4151, Aug. 1, 2000.
Khullar et al. "Nanoparticle Migration and Delivery of Paclitaxel to Regional Lymph Nodes in a Larch Animal Model," J Am Coll Surg. Mar. 2012; 214(3): 328-337.
Koay et al. "Intra-tumoral heterogeneity of gemcitabine delivery and mass transport in human pancreatic cancer," Phys Biol.; 11(6): 065002 2015.
Lapidus et al. "Anti-tumor effect of combination therapy with intratumoral controlled-release paclitaxel (Paclimer® Microspheres) and radiation," Prostate. 2004;58:291-298.
Lee et al. "In vivo efficacy of paclitaxel-loaded injectable in situ-forming gel against subcutaneous tumor growth," International Journal of Pharmaceutics 392 (2010) 51-56.
Linghu et al. "Feasibility of Endoscopic Ultrasound-Guided OncoGel (ReGel/Paclitaxel) Injection into the Pancreas in Pigs," Endoscopy 2005; 37 (11): 1140-1142.
Ma et al. "Paclitaxel Nano-Delivery Systems: A Comprehensive Review. J Nanomed Nanotechnol," 2013;4(2):1000164.
Matthes et al. "EUS-guided injection of paclitaxel (OncoGel) provides therapeutic drug concentrations in the porcine pancreas," Gastrointest Endosc. 2007;65(3):448-453.
Merisko-Liversidge et al. "Nanosizing: a formulation approach for poorly-water-soluble compounds," European Journal of Pharmaceutical Sciences 18 (2003) 113-120.
Miele et al. "Albumin-bound formulation of paclitaxel (Abraxane® ABI-007) in the treatment of breast cancer," International Journal of Nanomedicine 2009:4 99-105.
Morales et al. "Growth-inhibiting effects on intralesional docetaxel and paclitaxel on an experimental model of malignant neuroectodermal tumor," Journal of Neuro-Oncology 59:207-212, 2002.
Narang et al. "Pharmaceutical Development and Regulatory Considerations for Nanoparticles and Nanoparticulate Drug Delivery Systems," Journal of Pharmaceutical Sciences 2013.
Nsereko et al. "Localized delivery of paclitaxel in solid tumors from biodegradable chitin microparticle formulations," Biomaterials 23 (2002) 2723-2731.
Oh et al. "New treatment for cystic tumors of the pancreas: EUS-guided ethanol lavage with paclitaxel injection," Gastrointest Endosc. 2008;67(4):636-642.
Ranade et al. "Clinical and economic implications of the us of nanoparticle paclitaxel (Nanoxel) in India," Annals of Oncology 24 (Supplement 5): v6-v12, 2013.
Ruel-Gariepy et al. "A thermosensitive chitosan-based hydrogel for the local delivery of paclitaxel," European Journal of Pharmaceutics and Biopharmaceutics 57 (2004) 53-63.
Sanfilippo et al. "Phase I/II study of biweekly paclitaxel and radiation in androgen-ablated locally advanced prostate cancer," J Clin Oncol. 2008;26(18):2973-2978.
Shepard et al. "Phase II trial of neoadjuvant nab-paclitaxel in high risk patients with prostate cancer undergoing radical prostatectomy," J Urol. 2009;181:1672-1677.
Shikanov et al. "Intratumoral Delivery of Paclitaxel for Treatment of Orthotopic Prostate Cancer," Journal of Pharmaceutical Sciences, vol. 98, No. 3, Mar. 2009.
Surapaneni et al. "Designing Paclitaxel Drug Delivery Systems Aimed at Improved Patient Outcomes: Current Status and Challenges," ISRN Pharmacology, vol. 2012, Article ID 623139, 2012.
Swartz et al. "Lymphatic and interstitial flow in the tumor microenvironment: linking mechanobiology with immunity," Nature Reviews Cancer, vol. 12, Mar. 2012.
Van Soest et al. "Irrefutable evidence for the use of docetaxel in newly diagnosed metastatic prostate cancer: results from the STAMPEDE and CHAARTED trials," BMC Medicine (2015) 13:304.
Vukelja et al. "Phase 1 study of escalating-dose OncoGel (ReGel/paclitaxel) depot injection, a controlled-release formulation of paclitaxel, for local management of superficial solid tumor lesions Anticancer Drugs," 2007;18(3): 283-9.
Wang et al. "Intratumoral Injection of Taxol In Vivo Suppresses A549 Tumor Showing Cytoplasmic Vacuolization," Journal of Cellular Biochemistry 113:1397-1406 (2012).
Yoo et al. "An In Vivo Evaluation of Docetaxel Delivered Intratumorally in Head and Neck Squamous Cell Carcinoma," Arch Otolaryngol Head Neck Surg/vol. 131, May 2005.

(56) References Cited

OTHER PUBLICATIONS

Zentner et al. "Biodegradable block copolymers for delivery of proteins and water-insoluble drugs," Journal of Controlled Release 91 (2001) 203-215.

Zhao et al. "Preparation of superparamagnetic paclitaxel nanoparticles from modified chitosan and their cytotoxicity against malignant brain glioma," English Abstract, Journal of Biomedical Engineering Jun. 1, 2011, 28(3):513-516 (lang: chi).

Zhou et al. "Highly penetrative, drub-loaded nanocarriers improve treatment of glioblastoma," PNAS, Jul. 16, 2013, vol. 110, No. 29, 11751-11756.

The International Search Report (ISR) with Written Opinion for PCT/US2017/025718 dated Jun. 14, 2017, pp. 1-12.

Sharma, Shweta et al. "Development of stabilized Paclitaxel nanocrystals: In-vitro and in-vivo efficacy studies" European Journal of Pharmaceutical Sciences (2015) vol. 69, pp. 51-60.

Pathak, Pankaj et al. "Nanosized Paclitaxel Particles from Supercritical Carbon Dioxide Processing and Their Biological Evaluation" Langmuir (2007) vol. 23(5), pp. 2674-2679.

Shikanov et al: "Paclitaxel tumor biodistribution and efficacy after intratumoral injection of a biodegradable extended release implant", International Journal of Pharmaceutics, 358 (2008) 114-120.

Kakran Milali, el al., "Modified supercritical antisolvent method with enhanced mass transfer lo fabricate drug nanoparticles," Materials Science and Engineering, 33(5): 2864-2870, Mar. 2013.

Lee, el al., "Supercritical antisolvent production of biodegradable micro- and nanoparticles for controlled delivery of paclitaxel," Journal of Controlled Release, 125(2): 96-106, Oct. 2007.

International Search Report and Written Opinion for PCT/US2016/035993, dated Sep. 19, 2016.

Williamson, el al., "Phase I clinical trial of the intraperitoneal {IP} administration of a novel nanoparticle formulation of paclitaxel (NTX)," Poster Presentation, ACS, Sep. 2013.

U.S. Appl. No. 16/669,310, filed Oct. 30, 2019, Crititech, Inc.
U.S. Appl. No. 16/776,919, filed Jan. 30, 2019, Crititech, Inc.
U.S. Appl. No. 16/714,099, filed Dec. 13, 2019, Crititech, Inc.
U.S. Appl. No. 16/714,151, filed Dec. 13, 2019, Crititech, Inc.
U.S. Appl. No. 16/669,692, filed Oct. 31, 2019, Crititech, Inc.
U.S. Appl. No. 16/834,155, filed Mar. 30, 2020, Crititech, Inc.

* cited by examiner

METHODS FOR SOLID TUMOR TREATMENT

CROSS REFERENCE

This application is a continuation of U.S. patent application Ser. No. 16/512,044 filed Jul. 15, 2019, which is a continuation of Ser. No. 16/136,502 filed on Sep. 20, 2018, now U.S. Pat. No. 10,391,090 issued Aug. 27, 2019, which is a continuation of PCT application serial number PCT/US2017/025718 filed Apr. 3, 2017, which claims priority to U.S. Provisional Patent Application Ser. Nos. 62/318,014 filed Apr. 4, 2016 and 62/378,543 filed Aug. 23, 2016, each of which is incorporated by reference herein in their entirety.

BACKGROUND

Millions of patients are diagnosed each year world-wide as having cancer, and millions more die from cancer or cancer-related complications each year. The risk of cancer increases significantly with age, many cancers occur more commonly in developed countries, and cancer rates are increasing as life expectancy increases in the developed world. Current therapies include systemic treatments such as intravenous (IV) infusion injection of chemotherapeutic agents. These therapies, however, generally have significant undesired side effects to the patient due to systemic toxicity. Direct injection of chemotherapeutic agents into tumors has been attempted, however, the chemotherapeutic agents tend to "leak" out of the tumor especially when the chemotherapeutic agents are solubilized. Thus, improved methods for treating patients having cancer are needed.

SUMMARY OF THE INVENTION

In one aspect of the invention, disclosed is a method for treating a solid tumor, comprising administering to a subject with a solid tumor an amount effective of a composition comprising chemotherapeutic particles to treat the tumor, wherein the composition is directly injected into the tumor.

In another aspect of the invention, disclosed is a method for inhibiting tumor metastasis, comprising administering to a subject with a tumor an amount effective of a composition comprising chemotherapeutic particles to inhibit tumor metastasis.

In another aspect of the invention, disclosed is a suspension comprising chemotherapeutic particles, a pharmaceutically acceptable carrier, and a polysorbate.

In another aspect of the invention, disclosed is a kit comprising a first vial containing chemotherapeutic particles; a second vial containing a polysorbate; and instructions for reconstituting the chemotherapeutic particles into a suspension and for diluting the suspension with a diluent solution prior to administration to a patient.

Also disclosed in the context of the present invention are the following embodiments 1 to 77:

Embodiment 1 is a method for treating a solid tumor, comprising administering to a subject with a solid tumor an amount effective of a composition comprising chemotherapeutic particles to treat the tumor, wherein the composition is directly injected into the tumor, such as a malignant tumor.

Embodiment 2 is the method of embodiment 1 wherein the composition consists of the chemotherapeutic particles and a pharmaceutically acceptable carrier, such as a liquid carrier.

Embodiment 3 is the method of any one of embodiments 1-2, wherein the administering results in chemotherapeutic migrating into the lymphatic system of the subject.

Embodiment 4 is a method for inhibiting tumor metastasis, comprising administering to a subject with a malignant tumor an amount effective of a composition comprising chemotherapeutic particles to inhibit tumor metastasis.

Embodiment 5 is the method of embodiment 4, wherein the composition is directly injected into the tumor, or is peritumorally injected.

Embodiment 6 is the method of any one of embodiments 4-5, wherein the composition consists of the chemotherapeutic particles and a carrier (such as a liquid, semi-solid, or solid carrier).

Embodiment 7 is the method of any one of embodiments 1-3 and 6, wherein the carrier is an aqueous liquid carrier.

Embodiment 8 is the method of embodiment 7 wherein the aqueous liquid carrier is saline, such as normal saline.

Embodiment 9 is the method of any one of embodiments 1-8, wherein the composition is a suspension.

Embodiment 10 is the method of any one of embodiments 1-9 wherein the particles are (i) uncoated; (ii) not embedded, contained, enclosed or encapsulated within a solid excipient; and (iii) not microspheres, liposomes, or microcapsules containing chemotherapeutic and an excipient.

Embodiment 11 is the method of any one of embodiments 1-10, wherein the chemotherapeutic is selected from the group consisting of paclitaxel; derivatives of paclitaxel, docetaxel, cabazitaxel, taxanes; epithilones, Vinca alkaloids, such as vinblastine, vincristine, vindesine, vinorelbine; camptothecin analogs; epipodophyllotoxins, such as cisplatin, carboplatin, oxaliplatin, etoposide and teniposide; doxorubicin, anthrcyclines, 5-fluorouracil, topotecan, gemcitabine, peroxisome proliferator-activated receptor (PPAR) ligands, and antiangiogenics, or a pharmaceutically acceptable salt thereof.

Embodiment 12 is the method of any one of embodiments 1-11, wherein the chemotherapeutic is a taxane, or a pharmaceutically acceptable salt thereof.

Embodiment 13 is the method of any one of embodiments 1-12, wherein the chemotherapeutic is paclitaxel, or a pharmaceutically acceptable salt thereof.

Embodiment 14 is the method of any one of embodiments 1-13, wherein the tumor is selected from the group consisting of sarcomas, carcinomas, and lymphomas, breast tumors, prostate tumors, head and neck tumors, glioblastomas, bladder tumors, pancreatic tumors, liver tumors, ovarian tumors, colorectal tumors, cutaneous, lymphoid, and gastrointestinal tumors.

Embodiment 15 is the method of embodiment 13, wherein the tumor is selected from the group consisting of ovarian, bladder, breast, prostate, pulmonary, pancreatic, cutaneous, lymphoid, and gastrointestinal tumors.

Embodiment 16 is the method of embodiment 13, wherein the tumor is selected from the group consisting of ovarian and bladder tumors.

Embodiment 17 is the method of any one of embodiments 1-12, wherein the chemotherapeutic is docetaxel, or a pharmaceutically acceptable salt thereof.

Embodiment 18 is the method of embodiment 17, wherein the tumor is selected from the group consisting of ovarian, bladder, breast, and prostate tumors.

Embodiment 19 is the method of embodiment 17, wherein the tumor is selected from the group consisting of breast and prostate tumors.

Embodiment 20 is the method of any one of embodiments 1-19, wherein the chemotherapeutic particles comprise at least 95% chemotherapeutic and wherein the particles have a specific surface area (SSA) of at least 10 $m^2/g$, or at least 12 $m^2/g$, 14 $m^2/g$, 16 $m^2/g$, 18 $m^2/g$, 20 $m^2/g$, 25 $m^2/g$, 30 $m^2/g$, 32 $m^2/g$, 34 $m^2/g$, or 35 $m^2/g$.

Embodiment 21 is the method of embodiment 20, wherein the chemotherapeutic particles have an SSA of between about 10 $m^2/g$ and about 50 $m^2/g$.

Embodiment 22 is the method of any one of embodiments 20-21, wherein the chemotherapeutic particles have an SSA of:
(a) between 16 $m^2/g$ and 31 $m^2/g$ or between 32 $m^2/g$ and 50 $m^2/g$;
(b) between 16 $m^2/g$ and 30 $m^2/g$ or between 32 $m^2/g$ and 50 $m^2/g$;
(c) between 16 $m^2/g$ and 29 $m^2/g$ or between 32 $m^2/g$ and 50 $m^2/g$;
(d) between 17 $m^2/g$ and 31 $m^2/g$ or between 32 $m^2/g$ and 50 $m^2/g$;
(e) between 17 $m^2/g$ and 30 $m^2/g$ or between 32 $m^2/g$ and 50 $m^2/g$;
(f) between 17 $m^2/g$ and 29 $m^2/g$, or between 32 $m^2/g$ and 50 $m^2/g$;
(g) between 16 $m^2/g$ and 31 $m^2/g$ or between 33 $m^2/g$ and 50 $m^2/g$;
(h) between 16 $m^2/g$ and 30 $m^2/g$ or between 33 $m^2/g$ and 50 $m^2/g$;
(i) between 16 $m^2/g$ and 29 $m^2/g$ or between 33 $m^2/g$ and 50 $m^2/g$;
(j) between 17 $m^2/g$ and 31 $m^2/g$ or between 33 $m^2/g$ and 50 $m^2/g$;
(k) between 17 $m^2/g$ and 30 $m^2/g$ or between 33 $m^2/g$ and 50 $m^2/g$;
(l) between 17 $m^2/g$ and 29 $m^2/g$, or between 33 $m^2/g$ and 50 $m^2/g$;
(m) between 16 $m^2/g$ and 31 $m^2/g$, or ≥32 $m^2/g$;
(h) between 17 $m^2/g$ and 31 $m^2/g$, or ≥32 $m^2/g$;
(i) between 16 $m^2/g$ and 30 $m^2/g$, or ≥32 $m^2/g$;
(j) between 17 $m^2/g$ and 30 $m^2/g$, or ≥32 $m^2/g$;
(k) between 16 $m^2/g$ and 29 $m^2/g$, or ≥32 $m^2/g$;
(l) between 17 $m^2/g$ and 29 $m^2/g$, or ≥32 $m^2/g$;
(m) between 16 $m^2/g$ and 31 $m^2/g$, or ≥33 $m^2/g$;
(n) between 17 $m^2/g$ and 31 $m^2/g$, or ≥33 $m^2/g$;
(o) between 16 $m^2/g$ and 30 $m^2/g$, or ≥33 $m^2/g$;
(p) between 17 $m^2/g$ and 30 $m^2/g$, or ≥33 $m^2/g$;
(q) between 16 $m^2/g$ and 29 $m^2/g$, or ≥33 $m^2/g$; or
(r) between 17 $m^2/g$ and 29 $m^2/g$, or ≥33 $m^2/g$.

Embodiment 23 is the method of any one of embodiments 20-22, wherein the chemotherapeutic is paclitaxel, or a pharmaceutically acceptable salt thereof.

Embodiment 24 is the method of any one of embodiments 20-22, wherein the chemotherapeutic is docetaxel, or a pharmaceutically acceptable salt thereof.

Embodiment 25 is the method of any one of embodiments 1-24, wherein the chemotherapeutic particles include at least 95% by weight of a taxane, or a pharmaceutically acceptable salt thereof, wherein the particles have one or both of the following characteristics:
(i) a mean bulk density between about 0.050 $g/cm^3$ and about 0.15 $g/cm^3$, and/or
(ii) have a specific surface area (SSA) of at least 18 $m^2/g$, 20 $m^2/g$, 25 $m^2/g$, 30 $m^2/g$, 32 $m^2/g$, 34 $m^2/g$, or 35 $m^2/g$.

Embodiment 26 is the method of embodiment 25, wherein the taxane is selected from the group consisting of paclitaxel, docetaxel, cabazitaxel, taxadiene, baccatin III, taxchinin A, brevifoliol, and taxuspine D, or a pharmaceutically acceptable salt thereof.

Embodiment 27 is the method of embodiment 25, wherein the taxane is selected from the group consisting of paclitaxel, docetaxel, and cabazitaxel, or a pharmaceutically acceptable salt thereof.

Embodiment 28 is the method of embodiment 27, wherein the taxane is paclitaxel or a pharmaceutically acceptable salt thereof, and wherein the particles have a mean bulk density between about 0.050 $g/cm^3$ and about 0.12 $g/cm^3$, or between about 0.060 $g/cm^3$ and about 0.11 $g/cm^3$.

Embodiment 29 is the method of embodiment 27 or 28, wherein the taxane is paclitaxel or a pharmaceutically acceptable salt thereof, and wherein the paclitaxel particles have a specific surface area (SSA) of at least 18 $m^2/g$, 20 $m^2/g$, 25 $m^2/g$, 30 $m^2/g$, 32 $m^2/g$, 34 $m^2/g$, or 35 $m^2/g$.

Embodiment 30 is the method of any of embodiments 27-29, wherein the taxane is paclitaxel or a pharmaceutically acceptable salt thereof, and wherein the wherein the paclitaxel particles have a SSA of between about 22 $m^2/g$ and about 40 $m^2/g$, 25 $m^2/g$ and about 40 $m^2/g$, 30 $m^2/g$ and about 40 $m^2/g$, or between about 35 $m^2/g$ and about 40 $m^2/g$.

Embodiment 31 is the method of any one of embodiments 28-30, wherein the paclitaxel particles have a bulk density of between about 0.060 $g/cm^3$ and about 0.11 $g/cm^3$ and a SSA of between about 22 $m^2/g$ and about 40 $m^2/g$.

Embodiment 32 is the method of any one of embodiments 28-31, wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

Embodiment 33 is the method of embodiment 27, wherein the taxane is docetaxel or a pharmaceutically acceptable salt thereof, and wherein the particles have a mean bulk density between about 0.050 $g/cm^3$ and about 0.12 $g/cm^3$, or between about 0.06 $g/cm^3$ and about 0.1 $g/cm^3$.

Embodiment 34 is the method of embodiment 27 or 33, wherein the taxane is docetaxel or a pharmaceutically acceptable salt thereof, and wherein the docetaxel particles have a SSA of at least 18 $m^2/g$, 20 $m^2/g$, 25 $m^2/g$, 30 $m^2/g$, 35 $m^2/g$, 40 $m^2/g$, or 42 $m^2/g$.

Embodiment 35 is the method of embodiment 27 or 33-34, wherein the taxane is docetaxel or a pharmaceutically acceptable salt thereof, and wherein the docetaxel particles have a SSA of between about 40 $m^2/g$ and about 50 $m^2/g$, or between about 43 $m^2/g$ and about 46 $m^2/g$.

Embodiment 36 is the method of any one of embodiments 33-35, wherein the docetaxel particles have a bulk density of between about 0.06 $g/cm^3$ and about 0.1 $g/cm^3$ and a SSA of between about 40 $m^2/g$ and about 50 $m^2/g$.

Embodiment 37 is the method of any one of embodiments 33-36, wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

Embodiment 38 is the method of any one of embodiments 1-22, wherein the chemotherapeutic particles include at least 95% by weight of paclitaxel, or a pharmaceutically acceptable salt thereof, wherein the particles have a specific surface area (SSA) of at least 12 $m^2/g$.

Embodiment 39 is the method of embodiment 38, wherein the paclitaxel particles have a SSA of at least 12 $m^2/g$, 15 $m^2/g$, 20 $m^2/g$, 25 $m^2/g$, 30 $m^2/g$, 32 $m^2/g$, 34 $m^2/g$, or 35 $m^2/g$.

Embodiment 40 is the method of any one of embodiments 38-39, wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

Embodiment 41 is the method of any one of embodiments 1-22, wherein the chemotherapeutic particles include at least 95% by weight of paclitaxel, wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

Embodiment 42 is the method of any one of embodiments 1-22, wherein the chemotherapeutic particles include at least 95% by weight of docetaxel, wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

Embodiment 43 is the method of any one of embodiments 1-42, wherein the particles have a mean particle size number of between about 0.4 µm and about 1.2 µm, or between about 0.6 µm and about 1.0 µm.

Embodiment 44 is the method of any one of embodiments 1-43, wherein the particles are uncoated and the composition excludes polymers, proteins, polyethoxylated castor oil, and/or polyethylene glycol glycerides composed of mono-, di- and triglycerides and mono- and diesters of polyethylene glycol.

Embodiment 45 is the method of any one of embodiments 1-42, wherein the chemotherapeutic particle is present in a suspension further comprising a pharmaceutically acceptable aqueous carrier.

Embodiment 46 is the method of any one of embodiments 1-45, wherein the particles comprise at least 96%, 97%, 98%, 99%, or 100% of the compound.

Embodiment 47 is the method of any one of embodiments 1-46, wherein the chemotherapeutic particle is present in a suspension further comprising a polysorbate, such as polysorbate 80, wherein the polysorbate is present in the suspension at a concentration of between about 0.01% v/v and about 1.5% v/v, or between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v.

Embodiment 48 is the method of embodiment 47, wherein the chemotherapeutic is present in the suspension at a concentration between about 1 mg/ml and about 40 mg/ml, or about 6 mg/ml and about 20 mg/ml.

Embodiment 49 is the method of embodiment 48 wherein the chemotherapeutic particle comprises paclitaxel, or a pharmaceutically acceptable salt thereof, wherein the paclitaxel is present in the suspension at a concentration of between about 1 mg/ml and about 40 mg/ml, or about 6 mg/ml and about 20 mg/ml.

Embodiment 50 is the method of embodiment 48 wherein the chemotherapeutic particle comprises docetaxel, or a pharmaceutically acceptable salt thereof, wherein the paclitaxel is present in the suspension at a concentration of between about 1 mg/ml and about 40 mg/ml, or about 6 mg/ml and about 20 mg/ml.

Embodiment 51 is a suspension, comprising:
(a) chemotherapeutic particles;
(b) a pharmaceutically acceptable carrier; and
(c) a polysorbate, wherein the polysorbate is present in the suspension at a concentration of between about 0.01% v/v and about 1.5% v/v, or between about 0.01% v/v and about 1% v/v, about 0.01% v/v and about 0.5% v/v, about 0.01% v/v and about 0.4% v/v, about 0.05% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v.

Embodiment 52 is a kit, comprising:
(a) a first vial containing chemotherapeutic particles;
(b) a second vial containing a polysorbate and a pharmaceutically acceptable carrier;
(c) instructions for reconstituting the chemotherapeutic particles into a suspension by combining the contents of the first vial and the second vial, and for diluting the suspension with a diluent solution, such as 0.9% saline solution, prior to administration to a patient.

Embodiment 53 is the suspension of embodiment 51 or the kit of embodiment 52, wherein the chemotherapeutic particles are selected from the group consisting of paclitaxel; derivatives of paclitaxel, docetaxel, cabazitaxel, taxanes; epithilones, Vinca alkaloids, such as vinblastine, vincristine, vindesine, vinorelbine; camptothecin analogs; epipodophyllotoxins, such as cisplatin, carboplatin, oxaliplatin, etoposide and teniposide; doxorubicin, anthrcyclines, 5-fluorouracil, topotecan, gemcitabine, peroxisome proliferator-activated receptor (PPAR) ligands, and antiangiogenics, or a pharmaceutically acceptable salt thereof.

Embodiment 54 is the suspension or kit of any one of embodiments 51-53, wherein the chemotherapeutic is a taxane, or a pharmaceutically acceptable salt thereof.

Embodiment 55 is the suspension or kit of any one of embodiments 51-54, wherein the chemotherapeutic is paclitaxel, or a pharmaceutically acceptable salt thereof.

Embodiment 56 is the suspension or kit of any one of embodiments 51-54, wherein the chemotherapeutic is docetaxel, or a pharmaceutically acceptable salt thereof.

Embodiment 57 is the suspension of any one of embodiments 51 and 53-56, wherein the chemotherapeutic is present in the suspension at a concentration between about 1 mg/ml and about 40 mg/ml, or about 6 mg/ml and about 20 mg/ml.

Embodiment 58 is the suspension or kit of any one of embodiments 51-57, wherein the chemotherapeutic particles comprise at least 95% chemotherapeutic and wherein the particles have a specific surface area (SSA) of at least 10 $m^2/g$, or at least 12 $m^2/g$, 14 $m^2/g$, 16 $m^2/g$, 18 $m^2/g$, 20 $m^2/g$, 25 $m^2/g$, 30 $m^2/g$, 32 $m^2/g$, 34 $m^2/g$, or 35 $m^2/g$.

Embodiment 59 is the suspension or kit of any one of embodiments 51-58, wherein the chemotherapeutic particles have an SSA of between about 10 $m^2/g$ and about 50 $m^2/g$.

Embodiment 60 is the suspension or kit of any one of embodiments 51-59, wherein the chemotherapeutic particles have an SSA of:
(a) between 16 $m^2/g$ and 31 $m^2/g$ or between 32 $m^2/g$ and 50 $m^2/g$;
(b) between 16 $m^2/g$ and 30 $m^2/g$ or between 32 $m^2/g$ and 50 $m^2/g$;
(c) between 16 $m^2/g$ and 29 $m^2/g$ or between 32 $m^2/g$ and 50 $m^2/g$;
(d) between 17 $m^2/g$ and 31 $m^2/g$ or between 32 $m^2/g$ and 50 $m^2/g$;
(e) between 17 $m^2/g$ and 30 $m^2/g$ or between 32 $m^2/g$ and 50 $m^2/g$;
(f) between 17 $m^2/g$ and 29 $m^2/g$, or between 32 $m^2/g$ and 50 $m^2/g$;
(g) between 16 $m^2/g$ and 31 $m^2/g$ or between 33 $m^2/g$ and 50 $m^2/g$;
(h) between 16 $m^2/g$ and 30 $m^2/g$ or between 33 $m^2/g$ and 50 $m^2/g$;
(i) between 16 $m^2/g$ and 29 $m^2/g$ or between 33 $m^2/g$ and 50 $m^2/g$;

(j) between 17 m²/g and 31 m²/g or between 33 m²/g and 50 m²/g;
(k) between 17 m²/g and 30 m²/g or between 33 m²/g and 50 m²/g;
(l) between 17 m²/g and 29 m²/g, or between 33 m²/g and 50 m²/g;
(m) between 16 m²/g and 31 m²/g, or ≥32 m²/g;
(h) between 17 m²/g and 31 m²/g, or ≥32 m²/g;
(i) between 16 m²/g and 30 m²/g, or ≥32 m²/g;
(j) between 17 m²/g and 30 m²/g, or ≥32 m²/g;
(k) between 16 m²/g and 29 m²/g, or ≥32 m²/g;
(l) between 17 m²/g and 29 m²/g, or ≥32 m²/g;
(m) between 16 m²/g and 31 m²/g, or ≥33 m²/g;
(n) between 17 m²/g and 31 m²/g, or ≥33 m²/g;
(o) between 16 m²/g and 30 m²/g, or ≥33 m²/g;
(p) between 17 m²/g and 30 m²/g, or ≥33 m²/g;
(q) between 16 m²/g and 29 m²/g, or ≥33 m²/g; or
(r) between 17 m²/g and 29 m²/g, or ≥33 m²/g.

Embodiment 61 is the suspension or kit of any one of embodiments 51-60, wherein the chemotherapeutic particles include at least 95% by weight of a taxane, or a pharmaceutically acceptable salt thereof, wherein the particles have one or both of the following characteristics:
(i) a mean bulk density between about 0.050 g/cm³ and about 0.15 g/cm³, and/or
(ii) have a specific surface area (SSA) of at least 18 m²/g, 20 m²/g, 25 m²/g, 30 m²/g, 32 m²/g, 34 m²/g, or 35 m²/g.

Embodiment 62 is the suspension or kit of any one of embodiments 51-55 and 57-61, wherein the taxane is paclitaxel or a pharmaceutically acceptable salt thereof, and wherein the particles have a mean bulk density between about 0.050 g/cm³ and about 0.12 g/cm³, or between about 0.060 g/cm³ and about 0.11 g/cm³.

Embodiment 63 is the suspension or kit of any one of embodiments 51-55 and 57-62, wherein the taxane is paclitaxel or a pharmaceutically acceptable salt thereof, and wherein the paclitaxel particles have a specific surface area (SSA) of at least 12 m²/g, 18 m²/g, 20 m²/g, 25 m²/g, 30 m²/g, 32 m²/g, 34 m²/g, or 35 m²/g.

Embodiment 64 is the suspension or kit of any one of embodiments 51-55 and 57-63, wherein the taxane is paclitaxel or a pharmaceutically acceptable salt thereof, and wherein the wherein the paclitaxel particles have a SSA of between about 22 m²/g and about 40 m²/g, 25 m²/g and about 40 m²/g, 30 m²/g and about 40 m²/g, or between about 35 m²/g and about 40 m²/g.

Embodiment 65 is the suspension or kit of any one of embodiments 51-55 and 57-64, wherein the paclitaxel particles have a bulk density of between about 0.060 g/cm³ and about 0.11 g/cm³ and a SSA of between about 22 m²/g and about 40 m²/g.

Embodiment 66 is the suspension or kit of any one of embodiments 51-55 and 57-65, wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

Embodiment 67 is the suspension or kit of any one of embodiments 51-54 and 56-61, wherein the taxane is docetaxel or a pharmaceutically acceptable salt thereof, and wherein the particles have a mean bulk density between about 0.050 g/cm³ and about 0.12 g/cm³, or between about 0.06 g/cm³ and about 0.1 g/cm³.

Embodiment 68 is the suspension or kit of any one of embodiments 51-54, 56-61, and 67 wherein the taxane is docetaxel or a pharmaceutically acceptable salt thereof, and wherein the docetaxel particles have a SSA of at least 18 m²/g, 20 m²/g, 25 m²/g, 30 m²/g, 35 m²/g, 40 m²/g, or 42 m²/g.

Embodiment 69 is the suspension or kit of any one of embodiments 51-54, 56-61, and 67-68, wherein the taxane is docetaxel or a pharmaceutically acceptable salt thereof, and wherein the docetaxel particles have a SSA of between about 40 m²/g and about 50 m²/g, or between about 43 m²/g and about 46 m²/g.

Embodiment 70 is the suspension or kit of any one of embodiments 51-54, 56-61, and 67-69, wherein the docetaxel particles have a bulk density of between about 0.06 g/cm³ and about 0.1 g/cm³ and a SSA of between about 40 m²/g and about 50 m²/g Embodiment 71 is the suspension or kit of any one of embodiments 51-54, 56-61, and 67-70, wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

Embodiment 72 is the suspension or kit of any one of embodiments 51-71, wherein the particles have a mean particle size number of between about 0.4 μm and about 1.2 μm, or between about 0.6 μm and about 1.0 μm.

Embodiment 73 is the suspension or kit of any one of embodiments 51-72, wherein the particles are uncoated and the suspension or kit excludes polymers, proteins, polyethoxylated castor oil, and/or polyethylene glycol glycerides composed of mono-, di- and triglycerides and mono- and diesters of polyethylene glycol.

Embodiment 74 is the suspension or kit of any one of embodiments 51-73, wherein the pharmaceutically acceptable carrier is saline, such as 0.9% sodium chloride solution.

Embodiment 75 is the suspension or kit of any one of embodiments 51-74, wherein the polysorbate is polysorbate 80.

Embodiment 76 is the kit of any one of embodiments 52-75, wherein the contents of the first and second vial are sterile.

Embodiment 77 is the method, suspension, or kit of any one of embodiments 1-76, wherein the chemotherapeutic particles are non-agglomerated individual particles.

DETAILED DESCRIPTION OF THE INVENTION

Figure 1:
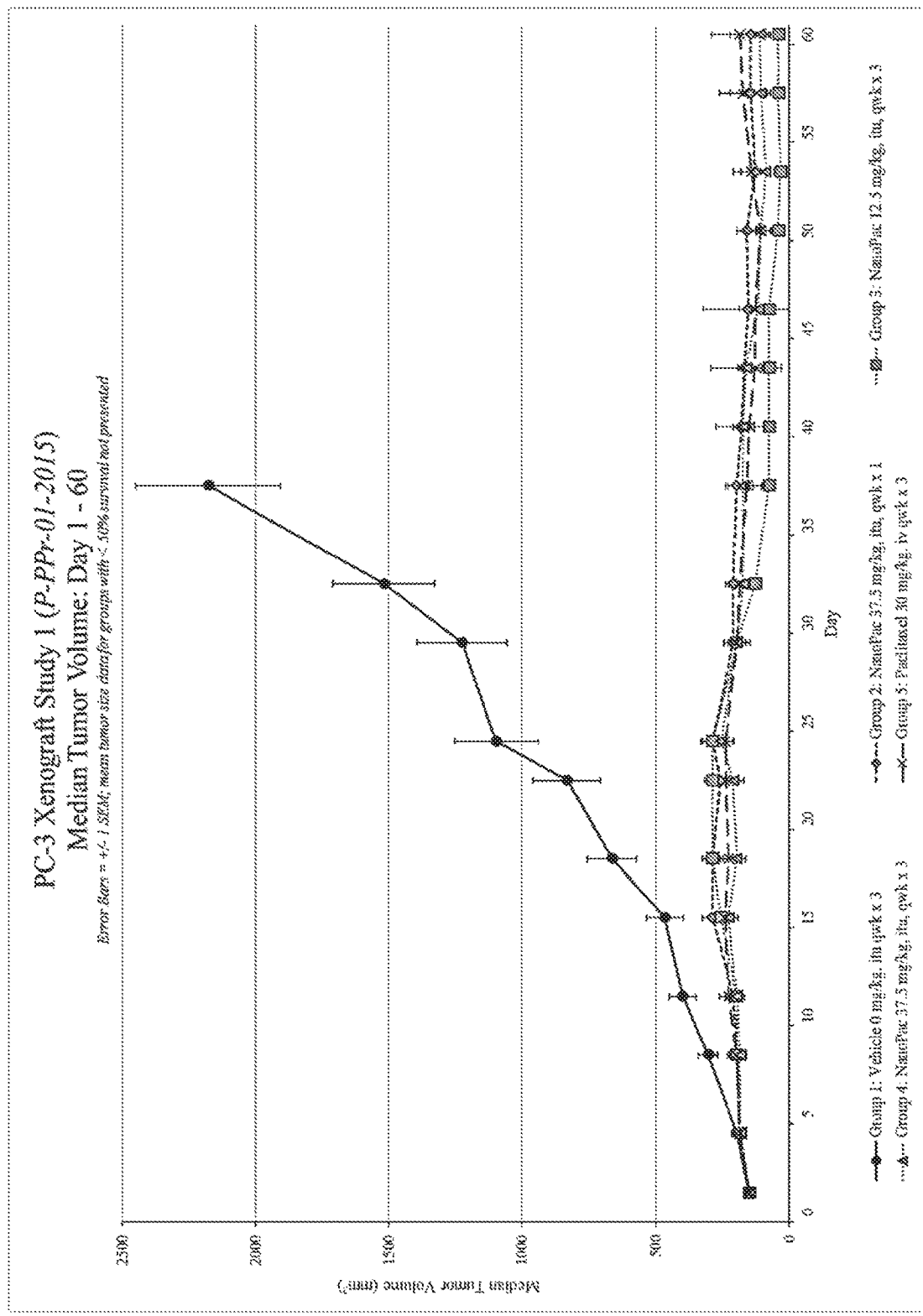
FIG. 1. Median tumor volume of PC3 human prostate carcinoma in mice treated by direct tumor injection (ITU) with vehicle and paclitaxel particles (Study P-PPr-01-2015).

As used herein, the singular forms "a", "an" and "the" include plural referents unless the context clearly dictates otherwise. "And" as used herein is interchangeably used with "or" unless expressly stated otherwise.

As used herein, "about" means +/–five percent (5%) of the recited unit of measure. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification. With respect to the phrase "consisting essentially of," a basic and novel property of the compositions of the present invention are their ability to treat solid tumors by direct injection of uncoated (neat) chemotherapeutic particles. This can be achieved without the use of coatings, encapsulations, and other drug delivery aids.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect, the invention provides methods for treating a solid tumor, comprising administering to a subject with a solid tumor an amount effective of a composition comprising chemotherapeutic particles to treat the tumor, wherein the composition is directly injected into the tumor. The inventors have surprisingly discovered that chemotherapeutic particles administered according to the methods of the invention can accumulate in very high levels in the tumor for an extended period of time with little leakage of the chemotherapeutic particles to undesired locations. As will be understood by those of skill in the art, free drug administered directly into tumors is inadequately retained in the tumor for entry into tumor cells for optimal therapeutic benefit. Thus, the methods of the invention provide a significant improvement over prior art methods. The chemotherapeutic particles exhibit a much higher surface area compared to chemotherapeutic particles prepared by typical procedures. This allows for the particles injected into the tumor to be too large to be carried away by systemic circulation and yet release the chemotherapeutic agent much faster than traditional particles.

As used herein, "chemotherapeutic particles" are particles consisting essentially of the chemotherapeutic (i.e.: at least 95%, 96%, 97%, 98%, 99%, or 100% chemotherapeutic) that are between 0.1 µm and 5 µm in diameter. Chemotherapeutic particles are different than "particles containing chemotherapeutic", which are particles that contain chemotherapeutic and at least one added excipient. Chemotherapeutic particles of the invention are uncoated, and are not embedded, contained, enclosed or encapsulated within a solid excipient. Chemotherapeutic particles of the invention may, however, contain impurities and byproducts typically found during preparation of the chemotherapeutic. Even so, chemotherapeutic particles comprise at least 95%, at least 96%, at least 97%, at least 98%, at least 99% or 100% chemotherapeutic, meaning the chemotherapeutic particles consist of or consist essentially of substantially pure chemotherapeutic.

In other embodiments, the chemotherapeutic particles are greater than 0.2 µm, or 0.3 µm in diameter. In another embodiment, the chemotherapeutic particles are at least 0.4 µm diameter. In further embodiments, the chemotherapeutic particles are between 0.4 µm and 2 µm in diameter, or between 0.5 µm and 1.5 µm in diameter, or between 0.2 µm and 1 µm in diameter, or between 0.2 µm to less than 1 µm in diameter. In further embodiments, the chemotherapeutic particles can have a mean particle size number of between in the range of about 0.4 µm to about 5 µm, about 0.4 µm to about 3 µm, about 0.5 µm to about 1.4 µm, about 0.4 µm to about 0.8 µm, about 0.4 µm to about 0.7 µm, or about 0.5 µm to about 0.7 µm. In a further embodiment, the chemotherapeutic or paclitaxel particles have a mean particle size number of between about 0.4 µm and about 1.2 µm, or between about 0.6 µm and about 1.0 µm. In another embodiment, the chemotherapeutic or paclitaxel particles have a mean particle size number of between 0.6 µm and 0.861 µm, or between about 0.5 µm to about 0.7 µm, or between about 0.2 µm to about 1 µm, or between about 0.2 µm to less than 1 µm, or between about 0.3 µm to about 1 µm, or between about 0.3 µm to less than 1 µm, or between about 0.4 µm to about 1 µm, or between about 0.4 µm to less than 1 µm.

Various processes are disclosed in U.S. Pat. Nos. 5,833,891 6,113,795, 8,221,779, and WO2016/197091, which are incorporated by reference herein in their entireties, for producing particle sizes as small as 0.1 to 5 µm for compounds.

As used herein, a "solid tumor" is an abnormal mass of tissue that usually does not contain cysts or liquid areas. Solid tumors may be benign (not cancer) or malignant (cancer). Different types of solid tumors are named for the type of cells that form them. Examples of solid tumors are sarcomas, carcinomas, and lymphomas. In one particular embodiment, the solid tumor is a malignant solid tumor.

As used herein, "directly injected into the tumor" means that some or all of the composition, such as a suspension, is injected into the tumor mass. As will be understood by those of skill in the art, such direct injection may include injection of some portion of the composition, such as a suspension, for example, drug on the periphery of the solid tumor ("peritumorally"), such as if the amount of composition or suspension thereof is too large to all be directly injected into the solid tumor mass. In one embodiment, the composition or suspension thereof is injected in its entirety into the solid tumor mass. As used herein the tumor includes both the tumor mass and tumor metastases, including but not limited to bone and soft tissue metastases.

As used herein, "treat" or "treating" means accomplishing one or more of the following: (a) reducing tumor size; (b) reducing tumor growth; (c) reducing or limiting development and/or spreading of metastases; (d) reducing or limiting development of one or more side effects of chemotherapy treatment.

Side effects of chemotherapy treatment include, but are not limited to anemia, neutropenia, thrombocytopenia, neurologic toxicities, reduction in appetite, constipation, diarrhea, hair loss, fatigue, nausea/vomiting, and pain.

In one embodiment, treating the tumor comprises inhibiting tumor metastasis. "Inhibiting" tumor cell metastasis may comprise any amount of inhibition compared to no treatment. In various non-limiting embodiments, the methods may comprise inhibiting development of tumor cell metastasis, or reducing existing tumor metastases by 5%, 10%, 25%, 50%; 100%, or more compared to control (such as no treatment).

In another aspect, the invention provides methods for inhibiting tumor metastasis, comprising administering to a subject with a tumor an amount effective of a composition comprising chemotherapeutic particles to inhibit tumor metastasis.

The inventors have surprisingly discovered that chemotherapeutic agents described herein administered to a subject migrate into, and are retained in, the lymphatic system of the subject. As will be understood by those of skill in the art, tumors are profused with circulating blood, and free drug administered directly into tumors is inadequately retained in the tumor for entry into tumor cells for optimal therapeutic benefit. Malignant cells within a tumor spread by way of the blood system, the lymphatic system to lymph nodes, by migration of cancer cells within the fluids of the peritoneal cavity, and to distant sites in a process known as metastasis. Thus, the methods of the invention can be used to inhibit metastasis. In this aspect, the chemotherapeutic particles can be administered via direct injection, intraperitoneal injection, peritumoral injection, or other suitable administrative route.

"Inhibiting" tumor cell metastasis may comprise any amount of inhibition compared to no treatment. In various non-limiting embodiments, the methods may comprise inhibiting development of tumor cell metastasis, or reducing existing tumor metastases, by 5%, 10%, 25%, 50%; 100%, or more compared to control (such as no treatment).

In various embodiments, the chemotherapeutic is selected from the group consisting of taxanes (paclitaxel, derivatives of paclitaxel, docetaxel, cabazitaxel, etc.), epithilones, Vinca alkaloids, such as vinblastine, vincristine, vindesine, vinorelbine; camptothecin analogs; epipodophyllotoxins, such as cisplatin, carboplatin, oxaliplatin, etoposide and teniposide; doxorubicin, anthrcyclines, 5-fluorouracil, topotecan, gemcitabine, peroxisome proliferator-activated receptor (PPAR) ligands, and antiangiogenics.

In various embodiments, the solid tumor is selected from the group consisting of sarcomas, carcinomas, and lymphomas, breast tumors, prostate tumors, head and neck tumors, glioblastomas, bladder tumors, pancreatic tumors, liver tumors, ovarian tumors, colorectal tumors, pulmonary, cutaneous, lymphoid, and gastrointestinal tumors. In a specific embodiment, the solid tumor is a prostate tumor and the chemotherapeutic particles are paclitaxel or docetaxel particles. In another specific embodiment, the solid tumor is an ovarian tumor and the chemotherapeutic particles are paclitaxel or docetaxel particles. In another specific embodiment, the solid tumor is a breast tumor and the chemotherapeutic particles are docetaxel particles. In another specific embodiment, the solid tumor is a pancreatic tumor and the chemotherapeutic particles are paclitaxel or docetaxel particles. In any of these embodiments, the tumor may be, for example, an adenocarcinoma.

The inventors have unexpectedly been able to produce chemotherapeutic particles, such as taxane particles, that have a mean bulk density between about 0.050 g/cm$^3$ and about 0.15 g/cm$^3$, and/or a specific surface area (SSA) of at least 18 m$^2$/g an SSA using novel methods for producing the particles as described below. As shown in the examples that follow, the increased specific surface area and decreased bulk density of the taxane particles result in significant increases in dissolution rate compared to the raw taxane and to milled taxane products used for comparison. Dissolution takes place only at a solid/liquid interface. Therefore, increased specific surface area will increase the dissolution rate due to a larger number of molecules on the surface of the particle having contact with the dissolution media. The bulk density takes into account the macrostructure and inter-particle space of a powder. Parameters that contribute to the bulk density include particle size distribution, particle shape, and the affinity of the particles for each other (i.e., agglomeration). Lower powder bulk densities yield faster dissolution rates. This is due to the ability of the dissolution media to more readily penetrate the interstitial or inter-particle spaces and have greater contact with the surface of the particles. Therefore, each of the increased specific surface area and the decreased bulk density result in the significant increase in dissolution rate for the taxane particles of the invention compared to the unprocessed or raw material, and the milled taxane product used for comparison. This provides a significant improvement for use of the taxane particles of the invention in, for example, tumor treatment.

Thus, in another embodiment, the chemotherapeutic particles have a specific surface area (SSA) of at least 10 m$^2$/g, or at least 12 m$^2$/g, 14 m$^2$/g, 16 m$^2$/g, 18 m$^2$/g, 20 m$^2$/g, 25 m$^2$/g, 30 m$^2$/g, 32 m$^2$/g, 34 m$^2$/g, or 35 m$^2$/g. In one embodiment, the chemotherapeutic particles have an SSA of between about 10 m$^2$/g and about 50 m$^2$/g.

In these embodiments, it is preferred that the chemotherapeutic particles are taxane particles. Taxanes are a class of diterpenoids containing a taxadiene core that are very poorly soluble in water. The taxane particles of the invention may be any suitable taxane, including but not limited to paclitaxel, docetaxel, cabazitaxel, taxadiene, baccatin III, taxchinin A, brevifoliol, and taxuspine D, combinations thereof, or pharmaceutically acceptable salts thereof. In one embodiment, the taxane is selected from the group consisting of paclitaxel, docetaxel, and cabazitaxel, or a pharmaceutically acceptable salt thereof. In various embodiments of the present invention, the taxane particles are uncoated (neat) individual particles; the taxane particles are not bound to or conjugated to any substance; no substances are absorbed or adsorbed onto the surface of the taxane particles; the taxane particles are not encapsulated in any substance; the taxane particles are not coated with any substance; the taxane particles are not microemulsions, nanoemulsions, microspheres, or liposomes of a taxane; and/or the taxane particles are not bound to, attached to, encapsulated in, or coated with a monomer, a polymer (or biocompatible polymer), a protein, a surfactant, or albumin. In some embodiments, a monomer, a polymer (or biocompatible polymer), a copolymer, a protein, a surfactant, or albumin is not absorbed or adsorbed onto the surface of the taxane particles. In some embodiments, the compositions are free of/do not include or contain a polymer/copolymer or biocompatible polymer/copolymer. In some embodiments, the compositions are free of/do not include or contain a protein. In some aspects of the invention, the compositions are free of/do not include or contain albumin. In some aspects of the invention, the compositions are free of/do not include or contain hyaluronic acid. In some aspects of the invention, the compositions are free of/do not include or contain a conjugate of hyaluronic acid and a taxane. In some aspects of the invention, the compositions are free of/do not include or contain a conjugate of hyaluronic acid and paclitaxel. In some aspects of the invention, the compositions are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), Vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), Poly (bis(P-carboxyphenoxy)propane-sebacic acid, poly(d,1-lactic acid) (PLA), poly(d,1-lactic acid-co-glycolic acid) (PLAGA), and/or poly(D, L lactic-co-glycolic acid (PLGA).

In one such embodiment, the chemotherapeutic particles include at least 95% by weight of a taxane, or a pharmaceutically acceptable salt thereof, wherein the particles have one or both of the following characteristics:

(i) a mean bulk density between about 0.050 g/cm$^3$ and about 0.15 g/cm$^3$, and/or (ii) have a specific surface area (SSA) of at least 18 m$^2$/g, 20 m$^2$/g, 25 m$^2$/g, 30 m$^2$/g, 32 m$^2$/g, 34 m$^2$/g, or 35 m$^2$/g.

As used herein, the "specific surface area" is the total surface area of the taxane particle per unit of taxane mass as measured by the Brunauer-Emmett-Teller ("BET") isotherm (i.e.: the BET SSA). As will be understood by those of skill in the art, the "taxane particles" can include both agglomerated taxane particles and non-agglomerated taxane particles; since the SSA is determined on a per gram basis it takes into account both agglomerated and non-agglomerated taxane particles in the composition. The BET specific surface area test procedure is a compendial method included in both the United States Pharmaceopeia and the European Pharmaceopeia.

As used herein, the bulk density of the taxane particles is the mass of the totality of particles in the composition divided by the total volume they occupy when poured into a graduated cylinder, without tapping the graduated cylinder. The total volume includes particle volume, inter-particle void volume, and internal pore volume.

In one embodiment, the taxane is paclitaxel or a pharmaceutically acceptable salt thereof, and the particles have a mean bulk density between about 0.050 g/cm$^3$ and about 0.12 g/cm$^3$. In another embodiment, the paclitaxel particles have a mean bulk density between about 0.060 g/cm$^3$ and about 0.11 g/cm$^3$. In some embodiments, the chemotherapeutic and taxane particles are non-agglomerated individual particles and are not clusters of multiple chemotherapeutic particles.

In a further embodiment, the taxane is paclitaxel or a pharmaceutically acceptable salt thereof, and the paclitaxel particles have a specific surface area (SSA) of at least 12 m$^2$/g. In various embodiments, the paclitaxel particles have an SSA of at least 12, 13, 14, 15, 16, 17, 18, 19, 20, 21, 22, 23, 24, 25, 26, 27, 28, 29, 30, 31, 32, 33, 34, 35, 36, 37, 38, 39, or at least 40 m$^2$/g. In various further embodiments, the paclitaxel particles have an SSA of between about 12 m$^2$/g and about 40 m$^2$/g, between about 14 m$^2$/g and about 40 m$^2$/g, between about 15 m$^2$/g and about 40 m$^2$/g, between about 16 m$^2$/g and about 40 m$^2$/g, between about 17 m$^2$/g and about 40 m$^2$/g, between about 18 m$^2$/g and about 40 m$^2$/g, between about 19 m$^2$/g and about 40 m$^2$/g, between about 20 m$^2$/g and about 40 m$^2$/g, between about 22 m$^2$/g and about 40 m$^2$/g, between about 25 m$^2$/g and about 40 m$^2$/g, between about 26 m$^2$/g and about 40 m$^2$/g, between about 30 m$^2$/g and about 40 m$^2$/g, between about 35 m$^2$/g and about 40 m$^2$/g, between about 20 m$^2$/g and about 29 m$^2$/g, between about 20 m$^2$/g and about 28 m$^2$/g, between about 20 m$^2$/g and about 26.2 m$^2$/g, between about 22 m$^2$/g and about 29 m$^2$/g, between about 22 m$^2$/g and about 28 m$^2$/g, between about 22 m$^2$/g and about 26.2 m$^2$/g, between about 32 m$^2$/g and about 40 m$^2$/g, between about 32 m$^2$/g and about 38 m$^2$/g, or between about 32 m$^2$/g and about 36 m$^2$/g.

In one preferred embodiment, the paclitaxel particles have a mean bulk density of between about between about 0.050 g/cm$^3$ and about 0.12 g/cm$^3$ and a SSA of at least 30 m$^2$/g. In another preferred embodiment, the paclitaxel particles have a mean bulk density of between about between about 0.050 g/cm$^3$ and about 0.12 g/cm$^3$ and a SSA of at least 35 m$^2$/g. In one the paclitaxel particles have a mean bulk density of between about between about 0.050 g/cm$^3$ and about 0.12 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of between about 30 m$^2$/g and about 40 m$^2$/g. In another preferred embodiment, the paclitaxel particles have a mean bulk density of between about 0.060 g/cm$^3$ and about 0.11 g/cm$^3$ and a SSA of at least 30 m$^2$/g. In a further embodiment, the paclitaxel particles have a mean bulk density of between about 0.060 g/cm$^3$ and about 0.11 g/cm$^3$ and a SSA of at least 35 m$^2$/g. These various embodiments are exemplified in the examples that follow.

In any of these various embodiments, the paclitaxel particles may include at least 4.16×10$^{-13}$ gram paclitaxel, or a pharmaceutically acceptable salt thereof per paclitaxel particle.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In another embodiment, the taxane is docetaxel or a pharmaceutically acceptable salt thereof, and the docetaxel particles have a mean bulk density between about 0.050 g/cm$^3$ and about 0.12 g/cm$^3$. In a further embodiment, the mean bulk density of the docetaxel particles is between about 0.06 g/cm$^3$ and about 0.1 g/cm$^3$.

In another embodiment, the taxane is docetaxel or a pharmaceutically acceptable salt thereof, and wherein the docetaxel particles have a SSA of at least 18 m$^2$/g. In various further embodiments, the docetaxel particles have a SSA of at least 20 m$^2$/g, 25 m$^2$/g, 30 m$^2$/g, 35 m$^2$/g, 40 m$^2$/g, or 42 m$^2$/g. In a further embodiment, the docetaxel particles have a SSA of between about 40 m$^2$/g and about 50 m$^2$/g. In another embodiment, the docetaxel particles have a SSA of between about 43 m$^2$/g and about 46 m$^2$/g.

In one preferred embodiment, the docetaxel particles have a mean bulk density between about 0.050 g/cm$^3$ and about 0.12 g/cm$^3$ and a SSA of at least 30 m$^2$/g. In another preferred embodiment, the docetaxel particles have a mean bulk density between about 0.050 g/cm$^3$ and about 0.12 g/cm$^3$ and a SSA of at least 35 m$^2$/g. In a further preferred embodiment, the docetaxel particles have a mean bulk density between about 0.050 g/cm$^3$ and about 0.12 g/cm$^3$ and a SSA of at least 40 m$^2$/g. In one preferred embodiment, the docetaxel particles have a mean bulk density between about 0.050 g/cm$^3$ and about 0.12 g/cm$^3$ and a SSA of between about 40 m$^2$/g and about 50 m$^2$/g. In another preferred embodiment, mean bulk density of the docetaxel particles is between about 0.06 g/cm$^3$ and about 0.1 g/cm$^3$ and the SSA is between about 40 m$^2$/g and about 50 m$^2$/g. These various embodiments are exemplified in the examples that follow.

In any of these various embodiments, the docetaxel particles may include at least $4.16 \times 10^{-13}$ grams docetaxel, or a pharmaceutically acceptable salt thereof per docetaxel particle.

In another embodiment, at least 20% (w/w) of the docetaxel is dissolved in 30 minutes or less in a solution of 15% methanol/85% water (v/v) in a USP II paddle apparatus operating at 75 RPM. A neutral pH was used where the solubility of the taxanes are not effected by pH. In another embodiment, the dissolution studies are carried out at 37° C.

In a further embodiment, the chemotherapeutic particles include at least 95% by weight of paclitaxel, or a pharmaceutically acceptable salt thereof, wherein the particles have a specific surface area (SSA) of:
(a) between 16 $m^2/g$ and 31 $m^2/g$ or between 32 $m^2/g$ and 40 $m^2/g$;
(b) between 16 $m^2/g$ and 30 $m^2/g$ or between 32 $m^2/g$ and 40 $m^2/g$;
(c) between 16 $m^2/g$ and 29 $m^2/g$ or between 32 $m^2/g$ and 40 $m^2/g$;
(d) between 17 $m^2/g$ and 31 $m^2/g$ or between 32 $m^2/g$ and 40 $m^2/g$;
(e) between 17 $m^2/g$ and 30 $m^2/g$ or between 32 $m^2/g$ and 40 $m^2/g$;
(f) between 17 $m^2/g$ and 29 $m^2/g$, or between 32 $m^2/g$ and 40 $m^2/g$;
(g) between 16 $m^2/g$ and 31 $m^2/g$ or between 33 $m^2/g$ and 40 $m^2/g$;
(h) between 16 $m^2/g$ and 30 $m^2/g$ or between 33 $m^2/g$ and 40 $m^2/g$;
(i) between 16 $m^2/g$ and 29 $m^2/g$ or between 33 $m^2/g$ and 40 $m^2/g$;
(j) between 17 $m^2/g$ and 31 $m^2/g$ or between 33 $m^2/g$ and 40 $m^2/g$;
(k) between 17 $m^2/g$ and 30 $m^2/g$ or between 33 $m^2/g$ and 40 $m^2/g$;
(l) between 17 $m^2/g$ and 29 $m^2/g$, or between 33 $m^2/g$ and 40 $m^2/g$;
(m) between 16 $m^2/g$ and 31 $m^2/g$, or $\geq 32$ $m^2/g$;
(h) between 17 $m^2/g$ and 31 $m^2/g$, or $\geq 32$ $m^2/g$;
(i) between 16 $m^2/g$ and 30 $m^2/g$, or $\geq 32$ $m^2/g$;
(j) between 17 $m^2/g$ and 30 $m^2/g$, or $\geq 32$ $m^2/g$;
(k) between 16 $m^2/g$ and 29 $m^2/g$, or $\geq 32$ $m^2/g$;
(l) between 17 $m^2/g$ and 29 $m^2/g$, or $\geq 32$ $m^2/g$;
(m) between 16 $m^2/g$ and 31 $m^2/g$, or $\geq 33$ $m^2/g$;
(n) between 17 $m^2/g$ and 31 $m^2/g$, or $\geq 33$ $m^2/g$;
(o) between 16 $m^2/g$ and 30 $m^2/g$, or $\geq 33$ $m^2/g$;
(p) between 17 $m^2/g$ and 30 $m^2/g$, or $\geq 33$ $m^2/g$;
(q) between 16 $m^2/g$ and 29 $m^2/g$, or $\geq 33$ $m^2/g$; or
(r) between 17 $m^2/g$ and 29 $m^2/g$, or $\geq 33$ $m^2/g$.

In another embodiment, at least 40% (w/w) of the paclitaxel, or a pharmaceutically acceptable salt thereof, in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In a further embodiment, the chemotherapeutic particles include at least 95% by weight of paclitaxel, or a pharmaceutically acceptable salt thereof, wherein at least 40% (w/w) of the paclitaxel is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In a further embodiment, the chemotherapeutic particles include at least 95% by weight of docetaxel, or a pharmaceutically acceptable salt thereof, wherein at least 20% (w/w) of the docetaxel is dissolved in 30 minutes or less in a solution of 15% methanol/85% water (v/v) in a USP II paddle apparatus operating at 75 RPM. pH 7 was used, and the solubility of the taxanes are not effected by pH. In another embodiment, the dissolution studies are carried out at 37° C.

In one embodiment, the chemotherapeutic particles comprises a dosage form of chemotherapeutic in suspension (i.e.: with a pharmaceutically acceptable carrier and any other components) of between about 0.1 mg/ml and about 100 mg/ml chemotherapeutic. In various further embodiments, the dosage form may be between about 0.5 mg/ml and about 100 mg/ml, about 1 mg/ml and about 100 mg/ml, about 2 mg/ml and about 100 mg/ml, about 5 mg/ml and about 100 mg/ml, about 10 mg/ml and about 100 mg/ml, about 25 mg/ml and about 100 mg/ml, about 0.1 mg/ml and about 75 mg/ml, about 0.5 mg/ml and about 75 mg/ml, about 1 mg/ml and about 75 mg/ml, about 2 mg/ml and about 75 mg/ml, about 5 mg/ml and about 75 mg/ml, about 10 mg/ml and about 75 mg/ml, about 25 mg/ml and about 75 mg/m, about 0.1 mg/ml and about 50 mg/ml, about 0.5 mg/ml and about 50 mg/ml, about 1 mg/ml and about 50 mg/ml, about 2 mg/ml and about 50 mg/ml, about 5 mg/ml and about 50 mg/ml, about 10 mg/ml and about 50 mg/ml, about 25 mg/ml and about 50 mg/m, about 0.1 mg/ml and about 25 mg/ml, about 0.5 mg/ml and about 25 mg/ml, about 1 mg/ml and about 40 mg/ml, about 1 mg/ml and about 25 mg/ml, about 2 mg/ml and about 25 mg/ml, about 5 mg/ml and about 25 mg/ml, about 10 mg/ml and about 25 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 10 mg/ml and about 15 mg/ml, about 0.1 mg/ml and about 10 mg/ml, about 0.5 mg/ml and about 10 mg/ml, about 1 mg/ml and about 10 mg/ml, about 2 mg/ml and about 10 mg/ml, about 5 mg/ml and about 10 mg/ml, about 0.1 mg/ml and about 5 mg/ml, about 0.5 mg/ml and about 5 mg/ml, about 1 mg/ml and about 5 mg/ml, about 2 mg/ml and about 5 mg/ml, about 0.1 mg/ml and about 2 mg/ml, about 0.5 mg/ml and about 2 mg/ml, about 1 mg/ml and about 2 mg/ml, about 0.1 mg/ml and about 1 mg/ml, about 0.5 mg/ml and about 1 mg/ml, about 0.1 mg/ml and about 0.5 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 3 mg/ml and about 8 mg/ml, or about 4 mg/ml and about 6 mg/ml paclitaxel, or at least about 0.1, 0.5, 1, 10, 20, 25, 50, 75, or 100 mg/ml chemotherapeutic.

In all aspects and embodiments of the invention, the composition may be provided in a suitable pharmaceutically acceptable carrier as deemed appropriate by attending medical personnel. In one embodiment, the formulation comprises a small volume (i.e.: 10 ul-40 ml; in other embodiments, 10 ul-35 ml, 10 ul-30 ml, 10 ul-25 ml, 10 ul-20 ml, 10 ul-15 ml, 10 ul-10 ml, 10 ul-7.5 ml, 10 ul-5 ml, 10 ul-4 ml, 10 ul-3 ml, 50 ul-40 ml, 50 ul-35 ml, 50 ul-30 ml, 50 ul-25 ml, 50 ul-20 ml, 50 ul-15 ml, 50 ul-10 ml, 50 ul-7.5 ml 50 ul-5 ml, 50 ul-4 ml, 50 ul-3 ml, 100 ul-40 ml, 100 ul-35 ml, 100 ul-30 ml, 100 ul-25 ml, 100 ul-20 ml, 100 ul-15 ml, 100 ul-10 ml, 100 ul-7.5 ml 100 ul-5 ml, 100 ul-5 ml, 100 ul-4 ml, 100 ul-3 ml, 500 ul-40 ml, 500 ul-35 ml, 500 ul-30 ml, 500 ul-25 ml, 500 ul-20 ml, 500 ul-15 ml, 500 ul-10 ml, 500 ul-7.5 ml, 500 ul-5 ml, 500 ul-4 ml, 500 ul-3 ml, 1 ml-40 ml, 1 ml-35 ml, 1 ml-30 ml, 1 ml-25 ml, 1 ml-20 ml, 1 ml-15 ml, 1 ml-10 ml, 1 ml-7.5 ml 1 ml-5 ml, 1 ml-4 ml, or 1 ml-3 ml).

Thus, in another aspect, the invention provides pharmaceutical compositions comprising a chemotherapeutic particle and a pharmaceutically acceptable carrier, where the total volume of the composition is between 1 ml and 40 ml, 1 ml and 35 ml, 1 ml and 30 ml, 1 ml and 25 ml, 1 ml and 20 ml, 1 ml and 15 ml, 1 ml and 10 ml, 1 ml and 7.5 ml, 1 ml and 5 ml, 1 ml and 4 ml, or 1 ml and 3 ml. In one embodiment, the composition consists of the chemotherapeutic particles and a pharmaceutically acceptable carrier, such as a liquid, semi-solid, or solid carrier.

In one embodiment, the composition comprises or consists of the chemotherapeutic particles and a liquid carrier. Any suitable liquid carrier may be used, such as an aqueous liquid carrier. Any suitable aqueous liquid carrier can be used, including but not limited to 0.9% saline solution (normal saline) such as 0.9% Sodium Chloride for Injection USP. In another embodiment, the composition comprises a suspension. In some embodiments, the suspension includes an aqueous carrier. The carrier can comprise buffering agent, osmotic salt and/or surfactant in water, and other agents for adjustment of pH, isotonicity and viscosity. In one embodiment employing an aqueous carrier, the concentration of surfactant is less than 1% on a w/w or w/v basis; in other embodiments, less than 0.5%, less than 0.25%, or about 0.1%. In other embodiments, the aqueous carrier can exclude the surfactants GELUCIRE® (polyethylene glycol glycerides composed of mono-, di- and triglycerides and mono- and diesters of polyethylene glycol) and/or CREMOPHOR® (polyethoxylated castor oil). In some embodiments, the composition or suspension excludes polymers, proteins (such as albumin), polyethoxylated castor oil, and/or polyethylene glycol glycerides composed of mono-, di- and triglycerides and mono- and diesters of polyethylene glycol.

The suspension can be administered as is or can be diluted with a diluent, e.g. with saline water (0.9% saline solution) optionally including a buffering agent and one or more other excipients, prior to administration. The diluent can be any liquid suitable for administration to a patient by injection. For example, the volume ratio of suspension to diluent might be in the range of 1:1-1:100 v/v or other suitable ratio.

In some embodiments, the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise chemotherapeutic particles, water, buffer and salt. It optionally further comprises a surfactant. In some embodiments, the suspension consists essentially of or consists of water, paclitaxel particles suspended in the water and buffer. The suspension can further contain an osmotic salt.

The suspension can comprise one or more surfactants. Suitable surfactants include by way of example and without limitation polysorbates, lauryl sulfates, acetylated monoglycerides, diacetylated monoglycerides, and poloxamers. Polysorbates are polyoxyethylene sorbitan fatty acid esters which are a series of partial fatty acid esters of sorbitol and its anhydrides copolymerized with approximately 20, 5, or 4 moles of ethylene oxide for each mole of sorbitol and its anhydrides. Non-limiting examples of polysorbates are polysorbate 20, polysorbate 21, polysorbate 40, polysorbate 60, polysorbate 61, polysorbate 65, polysorbate 80, polysorbate 81, polysorbate 85, and polysorbate 120. Polysorbates containing approximately 20 moles of ethylene oxide are hydrophilic nonionic surfactants. Examples of polysorbates containing approximately 20 moles of ethylene oxide include polysorbate 20, polysorbate 40, polysorbate 60, polysorbate 65, polysorbate 80, polysorbate 85, and polysorbate 120. Polysorbates are available commercially from Croda under the tradename TWEEN™. The number designation of the polysorbate corresponds to the number designation of the TWEEN, e.g., polysorbate 20 is TWEEN 20, polysorbate 40 is TWEEN 40, polysorbate 60 is TWEEN 60, polysorbate 80 is TWEEN 80, etc. USP/NF grades of polysorbate include polysorbate 20 NF, polysorbate 40 NF, polysorbate 60 NF, and polysorbate 80 NF. Polysorbates are also available in PhEur grades (European Pharmacopoeia), BP grades, and JP grades. The term "polysorbate" is a non-proprietary name. The chemical name of polysorbate 20 is polyoxyethylene 20 sorbitan monolaurate. The chemical name of polysorbate 40 is polyoxyethylene 20 sorbitan monopalmitate. The chemical name of polysorbate 60 is polyoxyethylene 20 sorbitan monostearate. The chemical name of polysorbate 80 is polyoxyethylene 20 sorbitan monooleate. In some embodiments, the suspension can comprise mixtures of polysorbates. In some embodiments, the suspension comprises polysorbate 20, polysorbate 40, polysorbate 60, polysorbate 65, polysorbate 80, polysorbate 85, and/or polysorbate 120. In other embodiments, the suspension comprises polysorbate 20, polysorbate 40, polysorbate 60, and/or polysorbate 80. In one embodiment, the suspension comprises polysorbate 80.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl) methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

In some embodiments, the chemotherapeutic particle is present in a suspension further comprising a polysorbate. In one specific embodiment, the chemotherapeutic particle is present in a suspension further comprising a polysorbate, wherein the polysorbate is polysorbate 80. In other embodiments, the polysorbate or polysorbate 80 is present in the suspension at a concentration of between about 0.01% v/v and about 1.5% v/v. The inventors have surprisingly discovered that the recited very small amounts of polysorbate 80 reduce the surface tension at the interface of the chemotherapeutic particles and the aqueous carrier in the suspension (such as saline). These embodiments are typically formulated near the time of use of the composition. In these embodiments, the particles are not coated with the polysorbate or polysorbate 80. In various other embodiments, the polysorbate or polysorbate 80 is present in the suspension at a concentration of between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v. In further embodiments, the chemotherapeutic, such as paclitaxel, is present in the suspension at a concentration between about 1 mg/ml and about 40 mg/ml, or about 6 mg/ml and about 20 mg/ml. In various further embodiments, the chemotherapeutic is present in the suspension at a concentration between about 6 mg/ml and about 15 mg/ml, between about 6 mg/ml and about 10 mg/ml, about 10 mg/ml and about 20 mg/ml, about 10 mg/ml and about 15 mg/ml, about 6 mg/ml, about 10 mg/ml, or about 15 mg/ml. In various further embodiments, the aqueous carrier in the composition may be saline, such as about 0.9% sodium chloride.

The present invention thus also provides a suspension comprising:
(a) chemotherapeutic particles;
(b) a pharmaceutically acceptable carrier; and
(c) a polysorbate, wherein the polysorbate is present in the suspension at a concentration of between about 0.01% v/v and about 1.5% v/v, or between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v.

In one embodiment, the polysorbate is polysorbate 80. In one embodiment, the pharmaceutically acceptable carrier is 0.9% saline solution. In another embodiment, the chemotherapeutic particles are taxane particles.

The present invention thus also provides kits, comprising:
(a) a first vial containing chemotherapeutic particles;
(b) a second vial containing a polysorbate and a pharmaceutically acceptable carrier; and
(c) instructions for reconstituting the chemotherapeutic particles into a suspension by combining the contents of the first vial and the second vial, and for diluting the suspension with a diluent solution, such as 0.9% saline solution, prior to administration to a patient.

In one embodiment, the polysorbate is polysorbate 80. In one embodiment, the pharmaceutically acceptable carrier is 0.9% saline solution. In one embodiment, the contents of the first and second vial are sterile. When the suspension of chemotherapeutic particles and polysorbate is diluted with the diluent solution, excessive dissolution of the chemotherapeutic particles is prevented.

The compositions, suspensions, and kits of this aspect of the invention can include any embodiment or combination of embodiments of the chemotherapeutic particles described herein, and any embodiment of the polysorbate or polysorbate 80 concentration described herein. In various further embodiments, the aqueous carrier in the composition may be saline, such as about 0.9% sodium chloride. The compositions, suspensions, and kits can exclude polymers, proteins (such as albumin), polyethoxylated castor oil, and/or polyethylene glycol glycerides composed of mono-, di- and triglycerides and mono- and diesters of polyethylene glycol.

The compositions and kits may further comprise other components as appropriate for a given chemotherapeutic particle. In one embodiment, a docetaxel particle may further comprise ethanol as a solvent; any suitable amount of ethanol may be used, such as between about 0.13% and 3.2% Dehydrated Alcohol (Ethanol), 200 proof, Undenatured, USP.

The subject may be any suitable subject that can benefit from the treatment, including but not limited to mammals (such as humans and other primates, dogs, cats, horses, cattle, pigs, sheep, goats, etc.)

The "amount effective" of the chemotherapeutic particle can be determined by an attending physician based on all relevant factors. The chemotherapeutic particles may be the sole chemotherapeutic administered, or may be administered with other therapeutics as deemed appropriate by an attending physician in light of all circumstances. In one embodiment, the methods further comprise treating the subject with the standard of care for the tumor being treated, such as intravenous chemotherapy, radiation therapy radiotherapy, surgical resection, etc. For example, the methods for treating prostate cancer may be combined with one or more of salvage prostatectomy, focal or whole-gland brachytherapy, cryotherapy, high-intensity focused ultrasound (HIFU), and stereo-tactic body radiotherapy (SBRT).

Direct injection of the chemotherapeutic particles into the tumor may be accomplished by any suitable means. In non-limiting embodiments, the injection may be carried out via magnetic resonance imaging-transrectal ultrasound fusion (MR-TRUS) guidance (such as for injecting prostate tumors), or via endoscopic ultrasound-guided fine needle injection (EUS-FNI).

Example 1

Production of Paclitaxel and Docetaxel Particles

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:

Ball size=5 mm
RPM=600
Processing time=60 min
Room temperature.

Preparation of Paclitaxel Particles

A solution of 65 mg/ml of paclitaxel was prepared in acetone. A BETE MicroWhirl® fog nozzle (BETE Fog Nozzle, Inc) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Paclitaxel nanoparticles produced had an average number-weighted mean size of 0.81 μm with an average standard deviation of 0.74 μm over three separate runs.

Preparation of Docetaxel Particles

A solution of 79.32 mg/ml of docetaxel was prepared in ethanol. The nozzle and a sonic probe were positioned in the pressurizable chamber approximately 9 mm (apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant. Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 μm Millipore filter and into the bottle. A background analysis was run to ensure the particle/mL count was below 100 particles/mL. A small amount of paclitaxel suspension, 5-100 μL, depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 μL, into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies

Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a U(V/V) is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 $m^2/g$. By comparison, the BET surface area of raw paclitaxel was measured at 7.25 $m^2/g$ (FIG. 2), while paclitaxel particles made according to the methods of U.S. Pat. Nos. 5,833,891 and 5,874,029 ranged from 11.3 to 15.58 $m^2/g$. Exemplary particle sizes produced using the methods of the invention are shown in Table 1.

TABLE 1

| | Surface area | Mean Size µm | | St Dev µm | |
|---|---|---|---|---|---|
| | $m^2/g$ | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density, SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

| Compound: Paclitaxel | | | | | |
|---|---|---|---|---|---|
| | | Particles | | | |
| Characteristic | Raw Material | Batch 1 | Batch 2 | Mean | Milled |
| Number Mean (um) | 1.16 | 0.83 | 0.67 | 0.75 | 0.89 |
| Volume Mean (um) | 1.29 | 1.42 | 0.57 | 1.00 | 1.35 |

TABLE 2-continued

| Compound: Paclitaxel | | | | | |
|---|---|---|---|---|---|
| | | Particles | | | |
| Characteristic | Raw Material | Batch 1 | Batch 2 | Mean | Milled |
| Bulk Density ($g/cm^3$) | 0.26 | 0.060 | 0.11 | 0.085 | 0.31 |
| Surface Area ($m^2/g$) | 10.4 | 35.6 | 39.8 | 37.7 | 15.0 |
| Dissolution (30 min) | 18% | 42% | 52% | 47% | 32% |

TABLE 3

| Compound: Docetaxel | | | | | |
|---|---|---|---|---|---|
| | | Particles | | | |
| Characteristic | Raw Material | Batch 1 | Batch II | Mean | Milled |
| Number Mean (um) | 1.58 | 0.92 | 0.80 | 0.86 | 1.11 |
| Volume Mean (um) | 5.05 | 4.88 | 4.03 | 4.46 | 3.73 |
| Bulk Density ($g/cm^3$) | 0.24 | 0.062 | 0.096 | 0.079 | 0.44 |
| Surface Area ($m^2/g$) | 15.9 | 43.0 | 45.4 | 44.2 | 15.2 |
| Dissolution (30 min) | 11% | 27% | 27% | 27% | 9% |

TABLE 4

| Paclitaxel Dissolution time course | | | |
|---|---|---|---|
| Timepoint (minutes) | Paclitaxel Raw Material | Paclitaxel Particles | Milled Paclitaxel |
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

| Docetaxel Dissolution time course | | | |
|---|---|---|---|
| Timepoint (minutes) | Docetaxel Raw Material | Docetaxel Particles | Milled Docetaxel |
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 120 | 22.4% | 38.9% | 13.6% |
| 225 | 26.8% | 43.1% | 16.0% |

Example 2

Pharmacokinetics and Tissue Distribution of Paclitaxel Particles Following Intraperitoneal Injection in Mice Purpose: This study was conducted to determine the level of absorption of paclitaxel from the peritoneal cavity into the systemic circulation following intraperitoneal delivery of a paclitaxel particle suspension. Tissue distribution of paclitaxel from the paclitaxel particle suspension following intraperitoneal administration was also evaluated.

Experimental Details: Female C57BL6 mice were inoculated with ID8 ovarian cancer cells and tumors were allowed to grow for 45 days. These mice were treated with paclitaxel particle suspension (36 mg/kg) in 0.9% saline via intraperitoneal administration in a total volume of 4 mL. Plasma and peritoneal fluid samples were collected at Time zero (pre-dose), 1, 6, 24 and 48 hours (at least four mice per time point) and paclitaxel in the plasma and peritoneal fluid was measured by LCMSMS. In addition, tissue samples were collected at Time zero (pre-dose), 1, 6, 24 and 48 hours post intraperitoneal administration of paclitaxel particles. Inguinal lymph nodes, peritoneal wall, ovary, liver, heart, kidney, lung, brain and tumor tissue samples from mice administered paclitaxel particles were analyzed by LC/MS/MS.

Results and Significance: The results of the paclitaxel levels in the plasma, peritoneal fluid and organ tissue samples are shown in the following table. Plasma paclitaxel remained at a very low level over the 48 hour period. The paclitaxel levels in the peritoneal fluid were much higher and demonstrated a substantial amount of variation. The limit of quantitation of the analytical method for paclitaxel was 0.01 µg/gm. The levels of paclitaxel in tissues inside the peritoneal cavity were consistently high as demonstrated by the results for the ovarian tumors, ovary, inguinal lymph nodes and peritoneal membrane. In contrast, the paclitaxel levels in tissues outside the peritoneal cavity were consistently lower as shown in the liver, heart, lung and brain tissues. These same results are shown in Table 6.

This data is significant because of the unexpectedly high levels of paclitaxel in the tissues that are in contact with the peritoneal fluid (ovarian tumors, ovary, inguinal lymph nodes and peritoneal membrane), and little paclitaxel to tissues not in contact with the peritoneal fluid. Based on these and other studies, the release of paclitaxel from the paclitaxel particles continues for several weeks and would be expected to provide a continuously high amount of paclitaxel, which would mean that the paclitaxel would accumulate in very high levels if injected directly into the tumor.

Example 3

Glioblastoma Study

In this study, we assessed the efficacy of paclitaxel particles against glioblastomas (GB). Nude mouse brains were injected with GB cells to establish primary tumors, which were injected after two weeks with paclitaxel particles. We monitored survival benefit against a control group that received only saline injections and a control group that has received Taxol™ (formulated in cremophor) injections. We delivered a dose of 100 mg/m$^2$ to the growing tumor by direct injection. The table below shows four different tumor sizes and the corresponding dose of paclitaxel particles of the invention, assuming a spherical shape for the tumor. As a control experiment Taxol™ formulated in cremophor and diluted in saline to the correct concentration was used.

TABLE 7

| Tumor Radius (mm) | Tumor Surface (mm$^2$) | ng of Nanotax per injection* | Dilution Factor** |
|---|---|---|---|
| 0.5 | 3.1 | 314.2 | 50 |
| 1 | 12.6 | 1256.6 | 13 |
| 1.5 | 28.3 | 2827.4 | 6 |
| 2 | 50.3 | 5026.5 | 3 |

*At a dose of 100 mg/m$^2$
**5 µl injection; Nanotax stock solution: 3,150 ng/µl At the highest dose of 5 µg of Paclitaxel per injection no toxicity was observed. Injected mice were kept alive for 8 to 9 days, after which no neurological symptoms were observed. After 9 days the mice were sacrificed and the brains harvested; the brains were dissected along the injection path and analyzed. Neither the paclitaxel particle group nor the Taxol™ group showed necrosis or lesions. Brain slices were used without further preparation to be analyzed with three different imaging technologies to create a composite image (data not shown):

TABLE 6

Summary Levels of Paclitaxel in chemotherapeutic particles-treated Mouse Tissue, Plasma and Peritoneal Fluid (values in µg/g) (4 animals)

| Time (hours) | Tumor (µg/g) | Ovary (µg/g) | Lymph (µg/g) | Membrane (µg/g) | Liver (µg/g) | Heart (µg/g) | Plasma (µg/ml) | IP Fluid (µg/ml) | Lung (µg/g) | Brain (µg/g) |
|---|---|---|---|---|---|---|---|---|---|---|
| 0 | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
|   | 0.0 | 0.00 | 0.00 | 0 | 0 | 0 | 0.0 | 0.0 | 0.00 | 0 |
| 1 | 458.6 | 500.00 | 190.80 | 107.23 | 7.0 | 0 | 0.5 | 49.0 | 1.97 | 0.04 |
|   | 180.1 | 263.64 | 199.28 | 31.42 | 6.7 | 0 | 0.0 | 1.0 | BQL | 0.13 |
|   | 135.3 | 498.00 | 122.90 | 9.38 | 3.1 | 0 | 0.0 | 0.7 | 2.78 | BQL |
|   | 158.1 | 1193.75 | 296.36 | 133.47 | 9 | 0 | 0.2 | 24.6 | 0.78 | 0.36 |
| 6 | 126.2 | 1068.97 | 486.87 | 64.8 | 48.8 | 0 | 0.0 | 1.2 | 1.18 | 0.11 |
|   | 240.0 | 816.33 | 648.15 | 91.38 | 46.6 | 0 | 0.4 | 40.4 | 1.65 | BQL |
|   | 701.2 | 751.05 | 48.86 | 132.35 | 27.0 | 0 | 0.0 | 1.8 | 0.75 | BQL |
|   | 89.7 | 211.20 | 143.33 | 97.41 | 14.3 | 0 | 0.0 | 4.2 | 1.56 | 0.08 |
| 24 | 81.3 | 502.70 | 90.14 | 27.09 | 41.3 | 0 | 0.0 | 1.5 | 5.22 | 0.29 |
|   | 204.5 | 1706.42 | 86.83 | 65.31 | 41.9 | 2.77 | 0.2 | 24.0 | 0.92 | 0.08 |
|   | 241.2 | 335.58 | 238.64 | 109.96 | 50.3 | 0 | 0.0 | 5.1 | 0.83 | 1.36 |
|   | 208.8 | 603.64 | 254.00 | 121.41 | 29.7 | 3 | BQ | BQ | 1.10 | 0.82 |
| 48 | 294.0 | 529.94 | 124.17 | 270.95 | 116.4 | 0 | 0.1 | 12.0 | BQL | 0.05 |
|   | 400 | 1389.83 | 1795.45 | 79.5 | 44.2 | 0 | 0.0 | 1.5 | BQL | 0.06 |
|   | 505.4 | 711.48 | 81.94 | 80.33 | 76.6 | 0 | 0.0 | 5.2 | BQL | 0.18 |
|   | 174.9 | 1272.11 | 224.88 | 218.24 | 34.0 | 0 | 0.2 | 28.6 | BQL | BQL |

(a) 2nd harmonic generation (SHG): Images appear in blue, mostly collagen and vessels and paclitaxel particles.
(b) Two-photon excitation fluorescence (TPEF): Images appear in green, mostly reactive cells, microglia, macrophages, some neuronal bodies.
(c) Coherent Anti-Stokes Raman Scattering (CARS): Images appear in red, tuned to —CH2 vibrations to look at lipids—mostly to myelin in the CNS, but also lipid droplet containing cells called foam cells will give a positive signal. Degenerating cells and macrophages with lipid vacuoles will also show up.

Due to the non-linear optical properties of the paclitaxel particle crystals the crystals can be seen directly with the second harmonic generation imaging technology. Clusters of paclitaxel particles were clearly visible at the injection site (i.e.: accumulated within the tumor) 9 days after injection in a mouse that was injected with 5 µg of paclitaxel particles and showed no neurological symptoms (data not shown).

Example 4

Prostate Cancer Studies

Two in vivo nonclinical pharmacology studies were conducted to determine the effects of intratumoral (ITU) delivery of paclitaxel particles in a nude mouse solid tumor PC-3 human prostate carcinoma nude mouse xenograft. In Study Number P-PPr-01-2015 mice were administered paclitaxel particles (also referred to as NanoPac™) at 37.5 mg/kg, qwk×1 (i.e.: a single dose); 12.5 mg/kg, qwk×3 (i.e.: a single dose three times per week); or 37.5 mg/kg, qwk×3; paclitaxel (30 mg/kg, qwk×3), or vehicle (0.1% w/v Polysorbate 80 in saline, qwk×3). Treatments with paclitaxel particles and vehicle were by ITU injection. Thirty-five days after cell implant, on D1 of the study, animals with individual tumor volumes of 108 to 196 mm3 were sorted into five groups (n=10) with group mean tumor volumes ranging from 150-153 mm3. All treatments were initiated on D1 of the study. Paclitaxel was administered as an IV infusion. All experimental treatments were tested in groups of 10 mice. Tumors were measured twice per week. Partial treatment outcome was based on percent tumor growth inhibition (% TGI), defined as the percent difference between the Day 32 median tumor volumes of treated and vehicle-control mice. The end of the experiment was a tumor volume of 2000 mm$^3$ or 60 days, whichever came first.

Paclitaxel particles were significantly active in the PC-3 prostate carcinoma model (FIG. 1). Treatment of animals with either a single dose or three weekly doses of paclitaxel particles resulted in identical survival extension and an increased number of study survivors/regressions when compared to vehicle-treated control animals. There was not a dose dependent response as dosing with paclitaxel particles at 12.5 or 37.5 mg/kg qwk×3 produced the maximum survival extension attainable in the study. Results for all paclitaxel particle-treated animals were well above the 60% TGI threshold indicative of potential therapeutic activity. IV-administered paclitaxel produced significant TGI and significantly improved survival extension in this study. All treatments were well-tolerated.

Study Number PD-PPr-02-2016 included docetaxel particles (also referred to as NanoDoce™) made as described above, as well as paclitaxel particles. Mice with PC-3 prostate carcinoma tumor xenografts were administered by ITU injection docetaxel particles at 100 mg/kg, qwk×1; 37.5 mg/kg, qwk×3; or 100 mg/kg, qwk×3; paclitaxel particles at 37.5 mg/kg, qwk×3; or vehicle (0.1% w/v Polysorbate 80 in saline, qwk×3) via IT injection; or were intravenously administered docetaxel (30 mg/kg, qwk×3). Twenty-six days after cell implant, on D1 of the study, animals with individual tumor volumes of 108 to 172 mm3 were sorted into five groups (n=10) with group mean tumor volumes ranging from 136-141 mm3. All treatments were initiated on D1 of the study. All experimental treatments were tested in groups of 10 mice. Tumors were measured twice per week. The end of the experiment was a tumor volume of 2000 mm$^3$ or 60 days, whichever came first. The maximum possible tumor growth delay (TGD) in this study was determined to be 41%.

Figure 2:
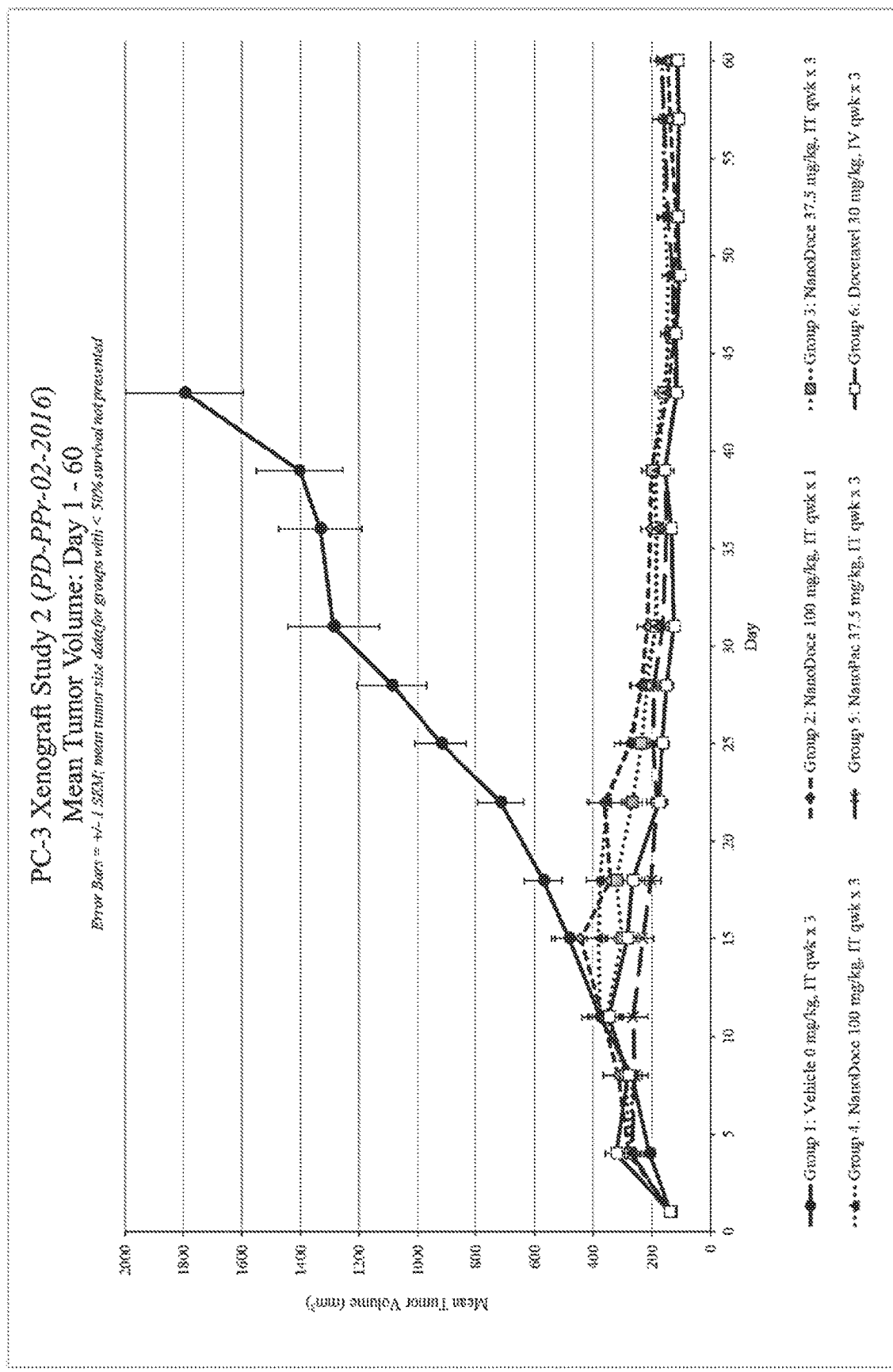
FIG. 2. Median tumor volume for mouse PC-3 prostate tumor xenografts treated IT with vehicle, NanoDoce™, NanoPac™ and treated IV with docetaxel (Study PD-PPr-02-2016).

Paclitaxel particles and docetaxel particles were highly active in the PC-3 prostate carcinoma model. All regimens, regardless of the dose/schedule, produced significant survival extension achieving in all cases the maximum possible TGD allowable in the study. Results for animals treated with paclitaxel particles, docetaxel particles, and docetaxel demonstrated similar levels of efficacy. All treatment regimens were well-tolerated. FIG. 2 shows mean tumor volume for mouse PC-3 prostate tumor xenografts treated IT with vehicle, NanoDoce, NanoPac and treated IV with docetaxel.

Example 5

MDA-MB-231 Breast Cancer Studies

The objective of this study was to determine the response of the subcutaneously (SC)-implanted MDA-MB-231 human breast cancer xenografts to treatment with paclitaxel particles ("NanoPac™") and docetaxel particles ("NanoDoce™"). Test articles were as shown in Table 8

TABLE 8

| Group | Test Article | Vehicle | Dose (mg/kg) | Dose Conc. (mg/mL) | Dose Volume |
|---|---|---|---|---|---|
| 1 | Vehicle | 0.1% T80/99.9% Sodium Chloride for Injection USP (0.9%) | 0 | 0 | 0.063*mL |
| 2 | NanoPac ™ | 0.1% T80/99.9% Sodium Chloride for Injection USP (0.9%) | 100 | 40 | 0.063*mL |
| 3 | NanoDoce ™ | 0.266% T80/2.66% ethanol/97.07% Sodium Chloride for Injection USP (0.9%) | 100 | 40 | 0.063*mL |
| 4 | Docetaxel | 7.5% ethanol/7.5% T80/85% Sodium Chloride for Injection USP (0.9%) | 30 | 3 | 10 mL/kg |
| 5 | Paclitaxel | 12.5% ethanol/12.5% Cremophor EL/75% Sodium Chloride for Injection USP (0.9%) | 30 | 3 | 10 mL/kg |

*Based on a 25 g mouse

Dose Formulation

NanoPac™: 0.75 mL of the 1% Polysorbate 80 ("T80") reconstitution solution was added into the vial of NanoPac™ (306 mg/vial). The reconstitution solution was prepared, sterile filtered through a 0.22 micron filter on the day of preparation, and stored refrigerated (2 to 8° C.) for no more than 7 days. The vial was vigorously hand shaken with inversion for 1 minute. Immediately after shaking, 6.9 mL of 0.9% Sodium Chloride for Injection USP was added to the vial to make a 40 mg/mL suspension (7.65 mL) and hand shaken the vial for another 1 minute. After mixing, the suspension was allowed to sit undisturbed for 5 minutes to reduce entrapped air and foam.

Handling: Room temperature.

Stability: Dose formulations were maintained at room temperature and considered stable for 8 hours.

NanoDoce™: 1.33 ml of the 1% T80/10% ethanol/in 0.9% saline reconstitution solution was added into the vial of NanoDoce particles (200 mg/vial). The reconstitution solution was prepared, sterile filtered through a 0.22 micron filter on the day of preparation, and stored refrigerated (2 to 8° C.) for no more than 7 days. The vial was vigorously hand shaken with inversions for 1 minute. Immediately after shaking, 2 ml of 0.9% Sodium Chloride for Injection USP was added and the vial was hand shaken for another 1 minute. An additional 1.67 ml of 0.9% Sodium Chloride for Injection USP was added to the vial and hand mixing with inversion continued for 1 minute. Final volume was 5 mL of a 40 mg/mL suspension. After mixing, the suspension was allowed to sit undisturbed for at least 5 minutes to reduce entrapped air and foam.

Handling: Room temperature.

Stability: Dose formulations were maintained at room temperature and considered stable for 8 hours.

Paclitaxel: Bulk Paclitaxel was added to the clinical formulation of Paclitaxel (6 mg/mL in 50% ethanol: 50% Cremophor EL) to make a 12 mg/mL solution and vortexed as needed. Sodium Chloride for Injection USP (0.9%) was added to make a 3 mg/mL solution of Paclitaxel and vortexed to mix.

Handling: Warm water.

Stability: Injected within 20 minutes of formulation.

Docetaxel: Sodium Chloride for Injection USP (0.9%) was added to make a 3 mg/mL solution of Docetaxel (20 mg/mL in 50% ethanol:50% T80) and vortexed to mix.

Handling: Room temperature.

Stability: Dose formulations were maintained at room temperature and considered stable for 8 hours.

Test System:

Species & Strain: Mouse; NCr-nu/nu

Supplier: Charles River Laboratories

Number on Study: Females—50

Study Design: A total of 88 female NCr-nu/nu mice were implanted with MDA-MB-231 breast tumor fragments from an in vivo passage subcutaneously (SC) on the right flank. The day of tumor cell implantation (Aug. 4, 2016) was designated as Day 0. Individual tumors of 50 animals grew to 100-221 mg in weight (100-221 mm$^3$ in size) on Day 13 after tumor cell implantation (Aug. 17, 2016), the day of treatment initiation/stage day (SD). Fifty animals were assigned to Groups 1-5 such that the mean tumor weights in all five groups on Day 13 were 147.4-149.6 mg (median tumor weights were 135-149 mg).

TABLE 9

| Group | No. of mice | Test Article | Dose Route/ Schedule | Dose (mg/kg) | Dose Conc. (mg/mL) | Dose Volume | Total Dose Delivered (mg) |
|---|---|---|---|---|---|---|---|
| 1 | 10 | Vehicle | IT*/qwk × 3 | — | — | 0.063 mL | 0 |
| 2 | 10 | NanoPac ™ | IT*/qwk × 3 | 100 | 40 | 0.063 mL | 7.56 |
| 3 | 10 | NanoDoce ™ | IT*/qwk × 3 | 100 | 40 | 0.063 mL | 7.56 |
| 4 | 10 | Docetaxel | IV/qwk × 3 | 30 | 3 | 10 mL/kg | 2.25** |
| 5 | 10 | Paclitaxel | IV/qwk × 3 | 30 | 3 | 10 mL/kg | 2.25** |

*IT = Intratumoral
**The total dose was based on a 25 g mouse.

The NanoPac™ and NanoDoce™ are suspensions. Prior to filling each syringe and between the injections of each animal, the test article was gently swirled/inverted. Intratumoral administration of the test material entailed the use of six needle tracks per tumor (27 G ½ inch needle). One sixth of the dose volume was injected as a slow bolus in each track, with ~15 seconds pause before removing the needle slowly, and moving to the next injection site spaced over the surface of the tumor. The animals were observed once daily for mortality and moribundity. The mice were weighed and the tumor measurements were taken twice weekly starting on the first day of treatment. Length and width were measured for each tumor. Tumor volume was determined using the formula for an ellipsoid sphere:

$$\text{Length} \times \text{Width}^2/2 = \text{Volume (mm}^3\text{)}$$

Figure 3:
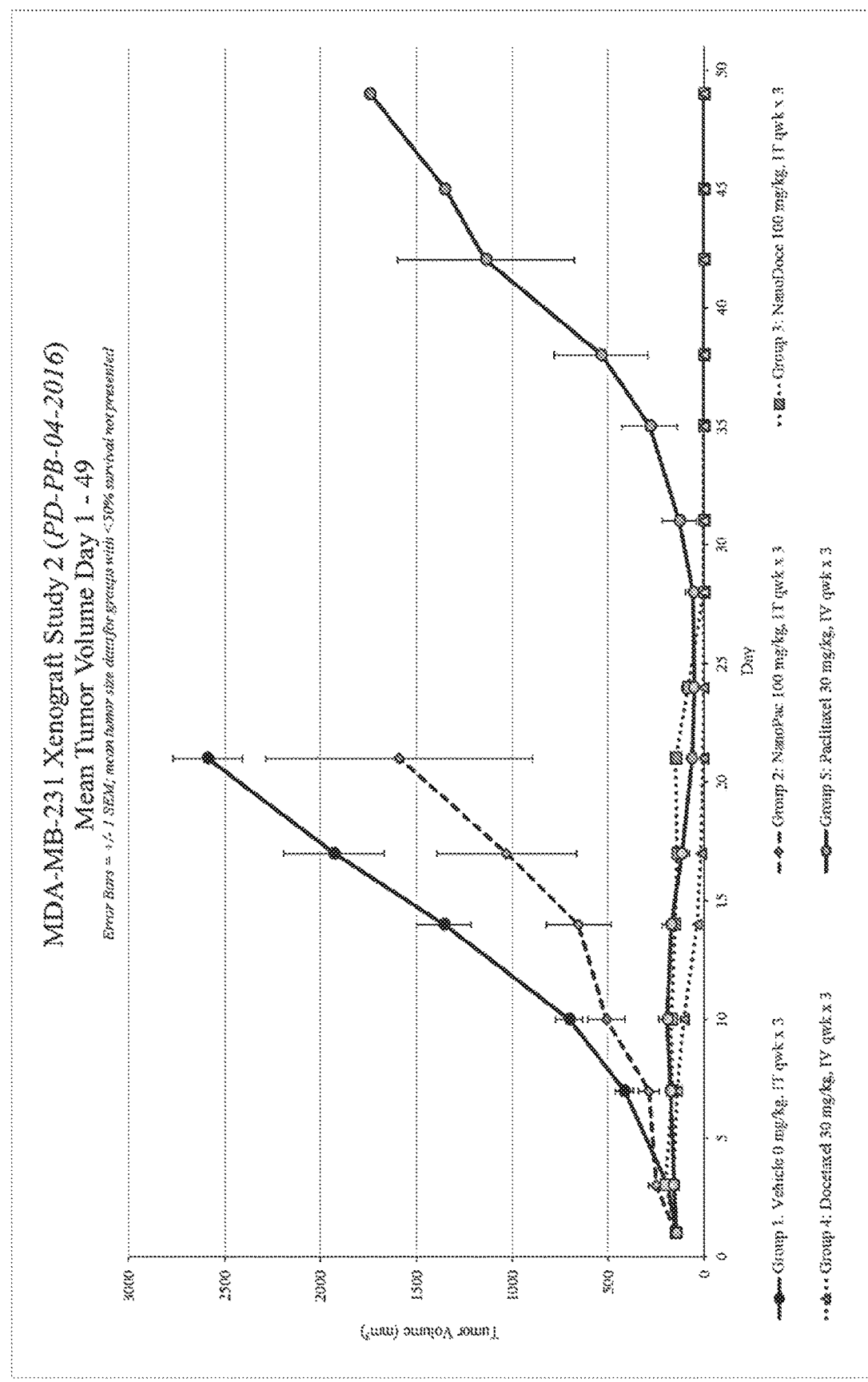
FIG. 3. Mean tumor volume for mouse MDA-MB-231 xenografts treated IT with vehicle, NanoDoce™, NanoPac™ and treated IV with docetaxel or paclitaxel (Study PD-PB-04-2016).

This formula was also used to calculate tumor weight, assuming unity density (1 mm$^3$=1 mg). Limit of tumor detection was 32 mg (4×4 mm). The experiment lasted for 61 days from the day of tumor implant. Animals whose weight decreased more than 30% from the weight on the first day of treatment or whose tumor reached 4,000 mg in weight, ulcerated, or sloughed off was euthanized prior to study termination. Comparisons between mean tumor volume after administration of test articles Docetaxel and NanoDoce™ and between Paclitaxel and NanoPac™ are presented in FIG. 3. More than 50% of animals in groups 1-2 were lost due to tumor ulceration, death, or large tumor size by day 21, and thus the mean data for these groups is not presented.

Results

The human MDA-MB-231 breast cancer xenografts in the vehicle-treated control group (Group 1) grew in all 10 mice to a mean tumor weight of 1,929 mg on Day 29 (n=9; the first measurement after the last day of treatment, 1 animal was removed on Day 22 due to ulceration). There were no animal deaths or mean body weight loss. Tumor inhibition was only compared to the control until Day 33 when there were 6 animals in the control group.

There were three animal deaths (Day 20 and 27) with three IT treatments (weekly) of NanoPac™ at a dose of 100 mg/kg (Group 2) and no mean body weight loss. The animal deaths occurred on days of IT injections. The repeated NanoPac™ treatment did not significantly inhibit the growth of the MDA-MB-231 breast cancer xenografts [mean tumor weight of 1,031 mg on Day 29 (n=7) corresponding to a % difference of −46.6% relative to the vehicle-treated control (p>0.05)]. The nadir of response occurred on Day 26 with a % difference of −51.8% which was significantly different than the vehicle-treated control group (p<0.05); Day 19 was also significantly different than the vehicle control group (p<0.05). There were two complete tumor regressions which remained tumor-free at the end of the study.

There were two animal deaths (Day 20 and 27) with the three IT treatments (weekly) of NanoDoce™ at a dose of 100 mg/kg (Group 3) and no mean body weight loss. The animal deaths occurred on days of IT injections. The repeated NanoDoce™ treatment significantly inhibited the growth of the MDA-MB-231 breast cancer xenografts [mean tumor weight of 143 mg on Day 29 (n=8) corresponding to a % difference of −92.6% relative to the vehicle-treated control (p<0.05)]. The tumor growth inhibition progressed to the nadir on Day 33 with a % difference of −94.2% (p<0.05); the mean tumor volume decreased to 0 on Day 40. The % difference was significant starting on Day 19 until no comparison was possible. The eight surviving animals remained tumor-free at the end of the study on Day 61.

There were no animal deaths following the three IV treatments (weekly) of docetaxel at a dose of 30 mg/kg (Group 4) with a mean body weight loss of 19.6% (4.78 g, Day 33). The repeated docetaxel treatment significantly inhibited the growth of the MDA-MB-231 breast cancer xenografts [mean tumor weight of 16 mg on Day 29 (n=10) corresponding to a % difference of −99.2% relative to the vehicle-treated control (p<0.001)]. The tumor growth inhibition progressed to the nadir on Day 33 with a % difference of −99.8% (p<0.05); the mean tumor volume decreased to 0 on Day 40. The % difference was significant starting on Day 19 until no comparison was possible. Complete tumor inhibition was observed on Day 40 when all 10 animals had completely regressed tumors which remained tumor-free at the end of the study. The docetaxel treated animals' tumor growth inhibition was significantly different than the NanoDoce™ treated animals' from Days 22-33 only.

Three IV treatments (weekly) with paclitaxel at a dose of 30 mg/kg (Group 5) were tolerated without animal deaths and no mean body weight loss. The paclitaxel treatment significantly inhibited the growth of the MDA-MB-231 breast cancer xenografts [mean tumor weight of 118 mg on Day 29 (n=10) corresponding to a % difference of −93.9% relative to the vehicle-treated control (p<0.05)]. The nadir of response occurred on Day 33 with a % difference of −97.4%. The % difference was significant starting on Day 19 until no comparison was possible. There were six complete tumor regressions with three tumor-free animals at the end of the study. The paclitaxel treated animals' tumor growth inhibition was significantly different than the NanoPac™ treated animals' Days 15 and 22-36.

Discussion

There were three or two animals dead in groups treated IT with NanoPac™ or NanoDoce™, respectively. The animal deaths occurred early and were not considered to be treatment related. The control group and treatment with paclitaxel or docetaxel was tolerated without animal deaths. Growth of the human MDA-MB-231 breast cancer xenografts was significantly inhibited by treatment with NanoDoce™ which had eight tumor-free surviving animals. Growth of the human MDA-MB-231 breast cancer xenografts was inhibited by treatment with docetaxel which had 10 tumor-free animals and was significantly different than NanoDoce™ treatment on Days 22-33. Growth of the human MDA-MB-231 breast cancer xenografts was not significantly inhibited by treatment with NanoPac™ on the day of evaluation but there was a significant difference on Days 19 and 21. Additionally, there were two tumor-free animals through day 49 (data not shown). Growth of the human MDA-MB-231 breast cancer xenografts was significantly inhibited by treatment with paclitaxel which was more effective than the NanoPac™ treatment on Days 15 and 22-36. On Day 49 there were three tumor-free animals in the IV paclitaxel treated group and two tumor-free animals in the IT NanoPac™ treated group. Growth of the human MDA-MB-231 breast cancer xenografts was significantly inhibited by treatment with docetaxel and NanoDoce™ On Day 49 there were ten tumor-free animals in the IV docetaxel treated group and eight tumor-free animals in the IT NanoDoce™ treated group.

Example 6

MX-1 Human Breast Cancer Xenograft Studies

The objective of this study was to determine the response of the subcutaneously (SC)-implanted MX-1 human breast cancer xenografts to treatment with paclitaxel particles (referred to as NanoPac™) and docetaxel particles (referred to as NanoDoce™). Test articles were as shown in Table 10:

TABLE 10

| Group | Test Article | Vehicle | Dose (mg/kg) | Dose Conc. (mg/mL) | Dose Volume (mL/kg) |
|---|---|---|---|---|---|
| 1 | Vehicle | 0.1% T80/99.9% Sodium Chloride for Injection USP (0.9%) | 0 | 0 | 0.063* mL |
| 2 | NanoPac ™ | 0.1% T80/99.9% Sodium Chloride for Injection USP (0.9%) | 100 | 40 | 0.063*mL |
| 3 | NanoDoce ™ | 0.2% T80/2% ethanol/18% PBS/79.8.% Sodium Chloride for Injection USP (0.9%)** | 100 | 40 | 0.063*mL |
| 4 | Docetaxel | 7.5% ethanol/7.5% T80/85% Sodium Chloride for Injection USP (0.9%) | 30 | 3 | 10 mL/kg |
| 5 | Paclitaxel | 12.5% ethanol/12.5% Cremophor EL/ 75% Sodium Chloride for Injection USP (0.9%) | 30 | 3 | 10 mL/kg |

*Based on a 25 g mouse
**Due to a calculation error, the Vehicle formulation for NanoDoce was incorrectly described in the Protocol (Appendix A) as 0.267% T80/2.67% ethanol/23.71% PBS/73.33% saline (0.9%).

Dose Formulations:

NanoPac™: 1) Add 0.75 mL of the 1% T80 reconstitution solution into the vial of NanoPac (306 mg/vial). Vigorously hand shake with inversion for 1 minute. 3) Immediately after shaking, add 6.9 mL of 0.9% Sodium Chloride for Injection USP to the vial to make a 40 mg/mL suspension (7.65 mL) and hand shake the vial for another 1 minute. After mixing, allow the suspension to sit undisturbed for 5 minutes to reduce entrapped air and foam.

Handling: Room temperature.

Stability: Dose formulations will be maintained at room temperature and considered stable for 8 hours.

NanoDoce™: 1) Add 1.0 ml of the 1% T80/10% ethanol/89% PBS reconstitution solution into the vial of NanoDoce particles (200 mg/vial). 2) Vigorously hand shake the vial with inversions for 1 minute. 3) Immediately after shaking, add 2 ml of 0.9% Sodium Chloride for Injection USP (0.9%) to the vial and hand shake the vial for another 1 minute. 4) Add an additional 2 ml of Sodium Chloride for Injection USP (0.9%) to the vial and continue hand mixing with inversion for 1 minute. Final volume 5 mL of 40 mg/mL NanoDoce suspension. After mixing, allow the suspension to sit undisturbed for at least 5 minutes to reduce entrapped air and foam.

Handling: Room temperature.

Stability: Dose formulations will be maintained at room temperature and considered stable for 8 hours.

Paclitaxel: 1) Add bulk paclitaxel to the clinical formulation of paclitaxel (6 mg/mL in 50% ethanol:50% Cremophor EL) to make a 12 mg/mL solution. Vortex as needed. 2) Add Sodium Chloride for Injection USP (0.9%) to make a 3 mg/mL solution of paclitaxel. Vortex to mix.

Handling: Warm water.

Stability: Inject within 20 minutes of formulation.

Docetaxel: 1) Add Sodium Chloride for Injection USP (0.9%) to make a 3 mg/mL solution of docetaxel (20 mg/mL in 50% ethanol:50% T80). Vortex to mix.

Test System:

Species & Strain: Mouse; NCr-nu/nu

Supplier: Charles River Laboratories

Number on Study: Females—50

Tumor model: A total of 88 female NCr-nu/nu mice were implanted with MX-1 breast tumor fragments from an in vivo passage subcutaneously (SC) on the right flank. The day of tumor cell implantation was designated as Day 0. Individual tumors of 50 animals grew to 100-198 mg in weight (100-198 $mm^3$ in size) on Day 10 after tumor cell implantation, the day of treatment initiation/Stage Day (SD). Fifty animals were assigned to Groups 1-5 such that the mean tumor weights in all five groups on Day 10 were 139.9 to 141.9 mg (median tumor weights were 135 or 144 mg).

Figure 4:
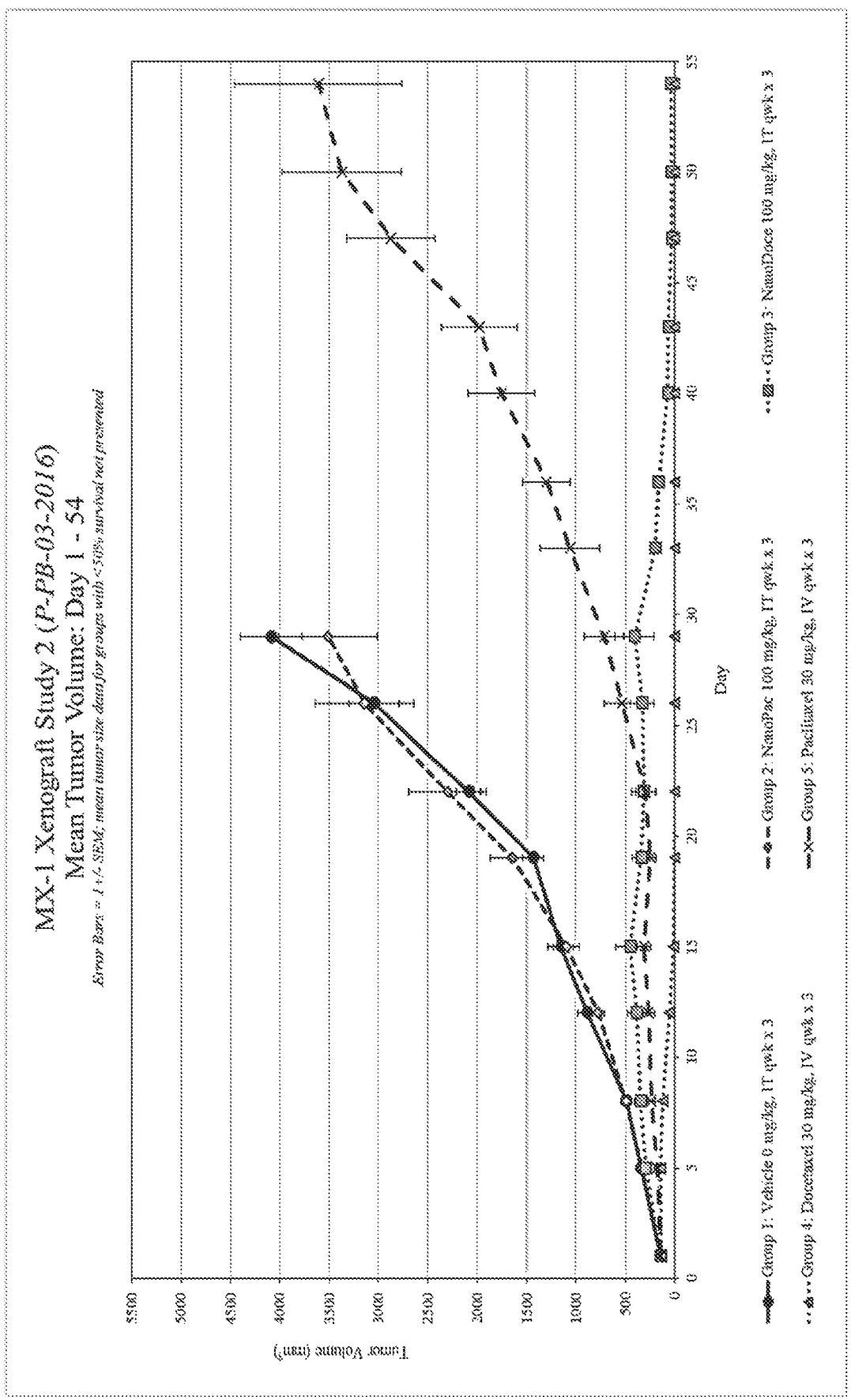
FIG. 4. Mean tumor volume for mouse MX-1 xenografts treated IT with vehicle, NanoDoce™, NanoPac™ and treated IV with docetaxel or paclitaxel (Study P-PB-03-2016).

The NanoPac™ and NanoDoce™ are suspensions. Prior to filling each syringe and between the injections of each animal, the test article was gently swirled/inverted. Animals were observed once daily for mortality and moribundity. Adverse signs were documented by exception only. Body weights were collected twice weekly beginning on SD. Tumor measurements were taken twice weekly beginning on SD, using a digital caliper. Length and width were measured for each tumor. Tumor volume was determined using the formula for an ellipsoid sphere: Length×Width$^2$/2=Volume ($mm^3$). This formula was also used to calculate tumor weight, assuming unity density (1 $mm^3$=1 mg). Limit of tumor detection is 32 mg (4×4 mm). The experiment lasted for 63 days from the day of tumor implant. Animals whose weight decreased more than 30% from the weight on the first day of treatment or whose tumor reached 4,000 mg in weight, ulcerated, or sloughed off was euthanized prior to study termination. Mean tumor volumes for each treatment are shown in FIG. 4. More than 50% of animals in groups 1-2 were lost due to tumor ulceration, death, or large tumor size by day 26, and thus the mean data for these groups is not presented.

Results

The human MX-1 breast cancer xenografts in the vehicle-treated control group (Group 1) grew in all 10 mice to a mean tumor weight of 1,153 mg on Day 24 (n=9; the last day of treatment). There was one death (Day 21) and one moribund animal euthanized (Day 25) with a mean body weight loss of 1.06% (0.26 g, Day 14). Tumor inhibition was only compared until Day 38 when there were 6 animals in the control group.

There were two animal deaths (Day 17 and 28) with three IT treatments (weekly) of NanoPac™ at a dose of 100 mg/kg (i.e., Group 2) and <1% mean body weight loss. The animal death on Day 17 occurred after the IT injection. The repeated NanoPac™ treatment did not significantly inhibit the growth of the MX-1 breast cancer xenografts [mean tumor weight of 1,096 mg on Day 24 (n=9) corresponding to a % difference of −4.9% relative to the vehicle-treated control (p>0.05)] The nadir of response occurred on Day 38 with a % difference of −14.1% which was not significantly different than the vehicle-treated control group (p>0.05).

There were two animal deaths (Day 17 and 24) during the three IT treatments (weekly) of NanoDoce™ at a dose of 100 mg/kg (i.e., Group 3) and no mean body weight loss. The animal deaths on Days 17 and 24 occurred after the IT injection. The repeated NanoDoce™ treatment significantly inhibited the growth of the MX-1 breast cancer xenografts [mean tumor weight of 449 mg on Day 24 (n=9) corresponding to a % difference of −61.0% relative to the vehicle-treated control (p<0.01)]. The tumor growth inhibi-

TABLE 11

| Group | No. of mice | Test Article | Dose Route/ Schedule | Dose (mg/kg) | Dose Conc. (mg/mL) | Dose Volume | Total Dose Delivered (mg) |
| --- | --- | --- | --- | --- | --- | --- | --- |
| 1 | 10 | Vehicle | IT*/qwk × 3 | — | — | 0.063 mL | 0 |
| 2 | 10 | NanoPac ™ | IT/qwk × 3 | 100 | 40 | 0.063 mL | 7.56 |
| 3 | 10 | NanoDoce ™ | IT/qwk × 3 | 100 | 40 | 0.063 mL | 7.56 |
| 4 | 10 | Docetaxel | IV/qwk × 3 | 30 | 3 | 10 mL/kg (0.10/10) | 2.25 |
| 5 | 10 | Paclitaxel | IV/qwk × 3 | 30 | 3 | 10 mL/kg (0.10/10) | 2.25 |

*IT = Intratumoral: use six needle tracks per tumor (27G ½ inch needle), inject one sixth of the volume as a slow bolus in each track, wait ~15 seconds then remove the needle slowly, space tracks over the surface of the tumor.

tion progressed to the nadir on Day 38 with a % difference of −90.1% (p<0.001); the mean tumor volume continued to decrease until Day 56. The % difference was significant starting on Day 17 until no comparison was possible. There were four complete tumor regressions with the animals remaining tumor-free at the end of the study.

There were two animals euthanized for body weight loss >30% (Day 24 and 31) following the three IV treatments (weekly) of docetaxel at a dose of 30 mg/kg (i.e., Group 4) with a mean body weight loss of 24.9% (5.90 g, Day 31). The repeated docetaxel treatment significantly inhibited the growth of the MX-1 breast cancer xenografts [mean tumor weight of 0.9 mg on Day 28 (n=9) corresponding to a % difference of −99.9% relative to the vehicle-treated control (p<0.001)]. The % difference was significant starting on Day 14 until no comparison was possible. Complete tumor inhibition was observed on Day 31 when all nine animals had completely regressed tumors. The eight surviving animals remained tumor-free at the end of the study on Day 63. The docetaxel treated animals' tumor growth inhibition was significantly different than the NanoDoce™ treated animals' from Days 14-52 but were not different from Day 56-63.

Three IV treatments (weekly) with paclitaxel at a dose of 30 mg/kg (i.e., Group 5) were tolerated without animal deaths and a mean body weight loss of 2.44% (0.59 g, Day 14). The paclitaxel treatment significantly inhibited the growth of the MX-1 breast cancer xenografts [mean tumor weight of 309 mg on Day 24 (n=10) corresponding to a % difference of −73.2% relative to the vehicle-treated control (p<0.001)]. The nadir of response occurred on Day 31 with a % difference of −86.0%. The % difference was significant starting on Day 14 until no comparison was possible. The paclitaxel treated animals' tumor growth inhibition was significantly different than the NanoPac™ treated animals' from Days 14-38 (the last day any mice remained in the NanoPac™ treated group.

Discussion:

There were two animals dead, moribund, or euthanized for weight loss in each group except for Paclitaxel treatment. Treatment with paclitaxel was tolerated without animal deaths. Growth of the human MX-1 breast cancer xenografts was significantly inhibited by IT treatment with NanoDoce™ which had four tumor-free surviving animals. Growth of the human MX-1 breast cancer xenografts was inhibited by IV treatment with docetaxel which had eight tumor-free surviving animals and was significantly different than NanoDoce™ treatment except at the end of the study (Days 56-63). Growth of the human MX-1 breast cancer xenografts was not significantly inhibited by treatment with NanoPac™. Growth of the human MX-1 breast cancer xenografts was significantly inhibited by treatment with paclitaxel which was more effective than the NanoPac™ treatment.

Example 7

JIMT-1 Human Breast Cancer Xenograft Studies

The objective of this study was to determine the response of the subcutaneously (SC)-implanted JIMT-1 human breast cancer xenografts to treatment with paclitaxel particles (referred to as Nanotax™). Test articles were as follows:
Procedures:
  100 CR female CB.17 SCID mice were injected with $1 \times 10^7$ JIMT-1 tumor cells in 50% Matrigel sc in flank. Cell Injection Volume was 0.1 mL/mouse.
  Age at Start Date: 8 to 12 weeks.

Performed a pair match when tumors reached an average size of 100-150 mm³, and began treatment. Test articles were as shown in Table 12:

TABLE 12

| Gr. | N | Regimen 1 Agent | mg/kg | Route | Schedule |
|---|---|---|---|---|---|
| 1[#] | 10 | vehicle | — | itu | qwk × 5 |
| 2 | 10 | Nanotax | 37.5 | itu | qwk × 1 |
| 3 | 10 | Nanotax | 12.5 | itu | qwk × 5 |
| 4 | 10 | Nanotax | 37.5 | itu | qwk × 5 |
| 5 | 10 | paclitaxel | 30 | iv | qwk × 3 |

[#]Control Group
paclitaxel = paclitaxel 5% Ethanol:5% Cremophor EL in D5W
Nanotax = Nanotax in 0.1% w/v Polysorbate 80 in Saline
vehicle = 0.1% w/v Polysorbate 80 in Saline
Dosing volume = 2.5 mL/kg (0.050 mL/20 g mouse). Adjust volume accordingly for body weight. For Group 5, IV paclitaxel, dosing volume was 10 mL/kg (0.20 mL/20 g mouse).

Body Weight: 5/2 (measure 5 days, off for 2 day) then biwk to end
Any individual animal with a single observation of >than 30% body weight loss or three consecutive measurements of >25% body weight loss was euthanized.
Endpoint TGD. Animals were monitored individually. The endpoint of the experiment was a tumor volume of 1000 mm³ or 60 days, whichever came first. When the endpoint is reached, the 25 animals were euthanized.

Tumor growth inhibition was evaluated on D29 (the last day of dosing for animals receiving 5 admins, G1, 3, 4) at 1000 mm³ and the study ended on D50 with a revised tumor volume endpoint of 600 mm³ for overall survival analysis.

The tumors were then collected from the 3 best responders in each group on day 50 for analysis to determine paclitaxel concentration in the tumor tissue. The timing of the analysis for each group relative to the last day of drug administration is as follows:
  21 days after last dose for groups 1, 3 and 4;
  49 days for group 2; and
  35 days for group 5.

These studies showed that Nanotax (NanoPac) was not significantly active in the JIMT-1 breast carcinoma model. Treatment of animals with five doses of Nanotax (NanoPac) resulted in small survival extensions and an increased number of study survivors when compared to vehicle-treated control animals. Results for all Nanotax (NanoPac)-treated animals were well below the 60% TGI threshold indicative of potential therapeutic activity. Paclitaxel produced significant TGI and significantly improved survival extension in this study. All treatments were well-tolerated.

Tissue processing was carried out as follows:
1. Control tumor tissue and tumor tissue samples were weighed and three volumes of water were added to each to yield samples with a dilution factor of 4.
2. Tumor tissues were homogenized with a homogenizer FastPrep®-24 using a speed of 4.0 msec for 100 sec.
3. 50 µL of control tumor tissue homogenate was added to separate wells of a 96 well plate for STDs, QC samples and blanks.
4. To the control tumor tissue homogenates, 50 µL of the appropriate solution was added for STDs and QC samples (50 µL of diluent was added for blanks)
5. For tumor tissue homogenate study samples, 50 µL of each sample was added to separate well of the 96-well plate and 50 µL aliquot of diluent was added to each tissue sample.

6. To all samples, 200 µL of internal standard (200 ng/mL Warfarin) solution in ACN was added.
7. The plate was vortexed vigorously for 10 minutes and then centrifuged for 10 minutes at 4000 rpm (Sorvall Legend X1R centrifuge, Thermo Scientific) at 15° C.
8. After centrifugation, 100 µL aliquots of supernatant were transferred to a new 96-well plate containing 100 µL of water in each well.
9. The plate was vortexed for approximately 1 minute and then aliquots were injected for LC/MS/MS analysis.

The results are shown in the Table 13:

Tumor Tissue Sample Concentrations

| Group | Animal | Part | Paclitaxel Concentration (ng/g) |
|---|---|---|---|
| 1 | 1 | 2 | BQL < 1 ng/g |
| 1 | 5 | 2 | BQL < 1 ng/g |
| 1 | 8 | 2 | BQL < 1 ng/g |
| 2 | 2 | 2 | 15300 |
| 2 | 5 | 2 | 3800 |
| 2 | 10 | 2 | 655000 |
| 3 | 1 | 2 | 1290000 |
| 3 | 6 | 2 | 1800 |
| 3 | 7 | 2 | 680 |
| 4 | 2 | 2 | 13400 |
| 4 | 6 | 2 | 1210 |
| 4 | 9 | 2 | 263 |
| 5 | 1 | 2 | BQL < 1 ng/g |
| 5 | 4 | 2 | BQL < 1 ng/g |
| 5 | 7 | 2 | BQL < 1 ng/g |

BQL: Below the quantitation limit of 1 ng/g before the dilution factor was applied.
Group 1: Vehicle (IT, qwk × 3)
Group 2: Nanotax (37.5 mg/kg, IT, qwk × 1)
Group 3: Nanotax (12.5 mg/kg, IT, qwk × 3)
Group 4: Nanotax (37.5 mg/kg, IT, qwk × 3)
Group 5: Paclitaxel (30 mg/kg, IV, qwk × 3)

This data surprisingly demonstrates that paclitaxel particles (groups 2, 3, and 4) persisted for very long time periods in the tumor.

Example 8

Female nude mice (NCr-nu/nu) with MDA-MB-231 breast tumor xenografts implanted on the right flank (PD-PB-04-2016; see above) were administered 100 mg/kg doses of NanoDoce® as intratumor injections on Days 13, 20 and 27 following tumor implant. On Day 61 following tumor implant, four Group 3 animals (100 mg/kg NanoDoce IT qwk×3) animals were necropsied and skin and underlying tissue at the tumor implant site were obtained. Tissues were homogenized in water. Aliquots of the homogenate were extracted with acetonitrile and extracts were analyzed by LC/UV/MS. A synthetic standard of docetaxel was used to compare the retention time (TR), UV and fragmentation pattern to the unknown compound present in the tissue samples. The analyses of tumor site tissue extracts indicated that docetaxel was present in two samples (Animals 3-7 and 3-8) of the four tissues examined. The LC/UV/MS analyses showed that the retention time (TR=16.6 min) and $MS^2$ spectra of the chromatographic peak within the extracted ion chromatogram (XIC) of m/z 807.7-808.7 obtained from the tissue extracts was similar to the authentic standard sample of docetaxel (TR=16.16 min).

In summary, based on similarity of retention time and mass spectral data with the authentic reference standard, it was confirmed that in two of four mouse breast tumor (MDA-MB-231) xenografts models administered intratumoral NanoDoce, the compound isolated from tumor implant site tissue samples was docetaxel.

Example 9

Phase IIa Dose Escalation Trial of Paclitaxel Particles (NanoPac™) Focal Therapy for Prostate Cancer in Subjects Undergoing Radical Prostatectomy

PROTOCOL SUMMARY

In this open-label, dose rising, Phase IIa trial with an expanded cohort at the dose of paclitaxel particles as described herein determined to have the best tolerability and safety profile, subjects with prostate cancer scheduled for prostatectomy will have paclitaxel particles injected under image guidance directly into the lobe of the prostate with the dominant lesion four weeks prior to prostatectomy. The study will include a dose escalation phase and a dose confirmation phase.

In the dose escalation phase, paclitaxel particle concentrations of 6, 10, and 15 mg/mL in an injection volume of up to 20% of the lobe of the prostate containing the dominant lesion will be studied in cohorts of three, with cohorts enrolled sequentially starting at the lowest concentration. Following Data Safety Monitoring Board (DSMB) review of the cohort data the next cohort may begin enrolling, an additional three at the current dose may be enrolled, or if the first dose does not provide adequate safety and tolerability the study may be halted. The dose determined to be the most suitable for further evaluation, defined as the highest dose with an acceptable safety and tolerability profile as determined by the DSMB, will enroll additional subjects to provide a cohort of 12 subjects at that dose level.

Tumor volume and serum prostate-specific antigen (PSA) will be determined prior to paclitaxel particle injection. Pharmacokinetic samples, PSA, and ejaculate will be collected in the interval between injection and prostatectomy. Imaging with multiparametric MRI (mpMRI) will be performed two to three weeks prior to paclitaxel particle (also referred to as NanoPac™) injection and prior to prostatectomy. Prostate and pelvic lymph nodes excised at prostatectomy will be evaluated.

Endpoints:
Primary endpoint: Safety and tolerability, as demonstrated by adverse events (AE), changes in laboratory assessments, physical examination findings, and vital signs.
Secondary endpoints:
  Concentration of paclitaxel in the systemic circulation post-injection and prior to prostatectomy;
  Presence of paclitaxel in the tumor within the prostate, the ipsilateral lobe of the prostate, the contralateral lobe of the prostate, and pelvic lymph nodes excised during prostatectomy;
  Tumor response (change in image volume on mpMRT; histologic evaluation via biopsy);
  Presence of tumor cells in the tumor within the prostate, the ipsilateral lobe of the prostate, the contralateral lobe of the prostate, and pelvic lymph nodes excised during prostatectomy.

Population: Up to a maximum of 30 men at a single site with adenocarcinoma of the prostate scheduled for radical prostatectomy.

Description of Study Agent: NanoPac™ (sterile paclitaxel particles) Powder for Suspension ("NanoPac") for direct injection into the lobe of the prostate containing the dominant lesion at concentrations of 6, 10, 15 mg/mL in an injection volume of up to 20% of the lobe of the prostate containing the dominant lesion.

Name and Description of Study Agent:

A formulation of particulate paclitaxel, identified as NanoPac™ (sterile particulate paclitaxel) Powder for Suspension, is manufactured using a Precipitation with Compressed Antisolvent (PCA) technique that employs supercritical carbon dioxide and acetone to generate paclitaxel nanoparticles within a well-characterized particle-size distribution. Following PCA, paclitaxel particles are filled into 60 mL Type 1, USP, clear-glass vials (306 mg/vial), each of which is closed with a bromobutyl rubber stopper and aluminum crimp seal, and sterilized by gamma irradiation. Prior to administration at the hospital/clinic, paclitaxel particles will be reconstituted with 1% Polysorbate 80, NF in 0.9% sodium chloride (saline) for Injection, USP, to form a suspension. The suspension will be further diluted with 0.9% sodium chloride for Injection, USP to achieve the final clinical formulation. This reconstitution and dilution will occur at the clinical site's pharmacy. The NanoPac concentration in the final clinical formulation will be either 6 mg/mL, 10 mg/mL, or 15 mg/mL. The final concentration of Polysorbate 80 is 0.1% in the 6 mg/mL suspension, 0.16% in the 10 mg/mL suspension, and 0.25% in the 15 mg/mL suspension.

Importance of the Study:

Prostate cancer is the second most common cancer in men, second only to non-melanoma skin cancer. Despite the high prevalence of the disease, it is a constantly-evolving area of medicine, presenting difficult decisions for patients and healthcare providers. At present, treatment for prostate cancer consists primarily of either of two options: active surveillance or radical whole-gland therapy. However, this dichotomy fails to reflect the heterogeneity of prostate cancer and the nuanced patient experience. Due, in part, to the widespread adoption of PSA as a screening tool, more men are being diagnosed with lower-risk, lower-grade cancer. Active surveillance may be an appropriate choice for some of these men, as radical whole-gland therapy risks life-altering consequences, such as impotence and incontinence. This is supported by the statistic that 49% of men undergoing radical prostatectomy are found to have only insignificant or indolent cancer. Nonetheless, prostate cancer has the fourth highest mortality rate of any cancer, and 73% of patients initially enrolled on active surveillance who ultimately undergo prostatectomy are found to have a significant cancer. As such, active surveillance not only risks disease progression, but can be psychologically distressing to patients.

Rationale:

This Phase IIa study will include patients with adenocarcinoma of the prostate scheduled to undergo a prostatectomy. The study design allows for a safety evaluation of direct injection of paclitaxel particles into the lobe of the prostate containing the dominant lesion as focal therapy prior to prostatectomy. We hypothesize that direct injection of paclitaxel particles into the prostate will result in limited, if any, systemic exposure to paclitaxel and should therefore result in only low-grade and transitory AE.

Direct injection, as opposed to intravenous (IV) administration, of paclitaxel particles would allow for higher concentrations of drug to target local disease with reduced systemic toxicity. Intraprostatic paclitaxel particles are expected to be more effective than IV paclitaxel due to prolonged intraprostatic residence and dissolution, resulting in continuous and greater paclitaxel concentrations in the tumor site. Subjects will have NanoPac™ injected under magnetic resonance imaging-transrectal ultrasound fusion (MR-TRUS) guidance directly into the lobe of the prostate containing the dominant lesion. Four weeks after injection of NanoPac™, the patient will undergo radical prostatectomy.

Prior to study entry, subjects will undergo ultrasound-guided prostate biopsy to diagnose and stage prostate cancer. This biopsy will be used to identify the dominant lesion, which is defined as the lesion with the highest Gleason score. The ultrasound performed during this biopsy will also be used to calculate the volume of the entire prostate. The volume of the lobe of the prostate containing the dominant lesion will be determined by calculating 50% of the total prostate volume as determined by ultrasound at the time of pre-study biopsy. The study will include a dose escalation phase and a dose confirmation phase.

Dose escalation: NanoPac™ concentrations of 6, 10, and 15 mg/mL in an injection volume of up to 20% of the lobe of the prostate containing the dominant lesion will be studied. Cohorts will be enrolled sequentially starting at the lowest concentration. Each cohort will have a planned minimum of three subjects. Data from the first three subjects in a cohort will be reviewed and evaluated by the DSMB. The outcome will be to determine whether to a) escalate to the next dose; b) add three additional subjects to the current dose; or c) expand the previous dose by three subjects.

Dose confirmation phase: Once the dose deemed appropriate for expansion and further evaluation has been determined, subjects will be enrolled to that dose to provide a total of 12 subjects dosed at that level. If two doses are similar, subjects will be enrolled to each of the doses; however, the total number of subjects treated will remain 12.

Standard of Care Study Procedures

The subjects being enrolled to this study will be undergoing a scheduled prostatectomy. Routine work-up prior to surgery, and the surgery itself, are considered standard of care. Follow-up to surgery will be per standard of care. Serum PSA will be determined prior to paclitaxel particle injection and weekly during the interval between paclitaxel particle injection and prostatectomy.

Imaging with ultrasound and mpMRI will have been conducted prior to study participation as part of the routine evaluation and confirmation of adenocarcinoma. These results will serve as the pre-treatment (or Baseline) data, prior to paclitaxel particle injection; another study-specific mpMRT will then be conducted within three days prior to prostatectomy, and ultrasound will be performed as part of the prostatectomy procedure.

In the interval between paclitaxel particle injection and prostatectomy, starting one week after injection, ejaculate will be collected on a weekly basis and evaluated for determination of paclitaxel concentration.

On the day of prostatectomy, after anesthesia has been administered, a biopsy will be performed. Immediately following biopsy, under the same anesthesia, subjects will have the scheduled prostatectomy and, following surgery, samples will be taken from the excised tissue (prostate and lymph nodes) for evaluation of paclitaxel concentration and for assessment of tumor cells, as described previously.

Example 10

Phase IIa Trial Evaluating the Safety of Intratumoral Injection of Paclitaxel Particles in Subjects with Locally Advanced Pancreatic Adenocarcinoma In this open-label Phase IIa trial, subjects with locally advanced pancreatic adenocarcinoma located in the tail or body of the pancreas will have completed at least one course of chemotherapy as part of Standard of Care (SOC). Once there is sufficient hematologic recovery, subjects will receive ITU paclitaxel particles (i.e., NanoPac™) via endoscopic ultrasound-guided direct injection. Subjects will be followed for overall survival (OS), progression-free survival (PFS), CA-19-9 levels, carcinoembryonic antigen (CEA) levels, reduction in pain, and tumor response to therapy (as shown by imaging).

Subjects will be enrolled in sequential, escalating cohorts of paclitaxel particles at concentrations of 6, 10, or 15 mg/mL injected directly into the tumor within the pancreas at up to 20% tumor volume (with a maximum of 5 mL volume being administered to any subject). The study will include a dose escalation phase and a dose confirmation phase.

Based on these tumor volume calculations, an amount of paclitaxel particles equal to 20% of tumor volume, not to exceed 5 mL in any subject, may be injected into the tumor particles into the tumor space and therefore resulting in prolonged paclitaxel exposure at the site of malignancy. Reduced clearance from the pancreas should result in lower systemic levels of paclitaxel, further limiting systemic toxicity.

The Phase IIa study will be carried out to evaluate the safety and tolerability of paclitaxel particles in up to 30 patients who will be undergoing chemotherapeutic treatment for locally advanced pancreatic adenocarcinoma located in the tail or body of the pancreas. In this clinical trial, paclitaxel particles will be administered directly into the pancreas via endoscopic ultrasound-guided fine needle injection (EUS-FNI).

The drug product is contained in a clear 60 mL Type 1, USP, clear-glass vial (306 mg/vial) as a powder fill of particulate paclitaxel, closed with a butyl rubber stopper and aluminum crimp seal, and sterilized by gamma irradiation. For clinical administration, the paclitaxel particle powder in vial is suspended with Sterile Reconstitution Solution (1% Polysorbate 80, NF in 0.9% Sodium Chloride for Injection, USP) and then further diluted with varying volumes of 0.9% Sodium Chloride for Injection, USP. The result is a 6, 10, or 15 mg/mL NanoPac suspension containing 0.1, 0.16, or 0.25% Polysorbate 80, NF, respectively, in 0.9% Sodium Chloride for Injection, USP.

TABLE 14

Components of NanoPac ® (sterile nanoparticulate paclitaxel) Powder for Suspension and final formulation

| Component | Function | Reference to Quality Standards | Amount |
|---|---|---|---|
| Components of NanoPac, Sterile Powder forSuspension | | | |
| Paclitaxel[a] | Active | USP | 306.0 mg/vial |
| Acetone [b] | Processing fluid | HPLC Grade | [b] |
| Carbon Dioxide [b] | Processing fluid | ISBT Beverage Grade 99.9% pure | [b] |
| Components of NanoPac, Final Formulation | | | |
| Paclitaxel[a] | Active | USP | 306.0 mg/vial |
| Polysorbate 80 | Surfactant | NF | 0.1% (6 mg/mL NanoPac) |
| | | | 0.16% (10 mg/mL NanoPac) |
| | | | 0.25% (15 mg/mL NanoPac) |
| 9% Sodium Chloride for Injection | Suspension solution | USP | 51 mL (6 mg/mL NanoPac) |
| | | | 30.6 mL (10 mg/mL NanoPac) |
| | | | 20.4 mL (15 mg/mL NanoPac) |

[a] In nanoparticulate form.
[b] Removed during processing.

The paclitaxel particles for use in the study (referred to as NanoPac™) are manufactured by CritiTech, Inc. (Lawrence, Kans.) using a Precipitation with Compressed Antisolvent (PCA) technique that employs supercritical carbon dioxide and acetone to generate paclitaxel nanoparticles within a well-characterized particle-size distribution. Prior to administration at the hospital/clinic, the paclitaxel particle powder in vial is suspended with Sterile Reconstitution Solution (1% Polysorbate 80, NF in 0.9% Sodium Chloride for Injection, USP) and then further diluted with 0.9% Sodium Chloride for Injection, USP, resulting in a 6, 10, or 15 mg/mL NanoPac™ suspension.

Introduction of the particulate paclitaxel suspension into the site of the malignancy is hypothesized to create a depot of paclitaxel within the affected area (in this case, the pancreatic tumor), slowly releasing the paclitaxel from the Endpoints: Primary endpoint: Safety and tolerability as demonstrated by adverse events (AE), changes in laboratory assessments, physical examination findings and vital signs.

Secondary endpoints:

Concentration of paclitaxel in the systemic circulation post-injection (as determined by PK analysis);

Tumor response (RECIST as per Eisenhauer et al. 2009);

Reduction in pain (as measured by the visual analog scale [VAS]);

Change in tumor marker CA19-9;

Change in tumor marker CEA.

Population: Up to 30 subjects with locally advanced pancreatic adenocarcinoma located in the tail or body of the pancreas.

We claim:

1. A method for treating a solid tumor, comprising administering to a subject with a solid tumor an amount effective of a composition comprising taxane particles to treat the tumor, wherein the composition is directly injected into the tumor, wherein the taxane particles comprise at least 95% taxane or a pharmaceutically acceptable salt thereof, wherein the taxane particles have a specific surface area (SSA) of at least 18 m$^2$/g.

2. The method of claim 1 wherein the composition consists of the taxane particles and a pharmaceutically acceptable carrier.

3. The method of claim 2, wherein the carrier is an aqueous liquid carrier.

4. The method of claim 3 wherein the aqueous liquid carrier is saline.

5. The method of claim 1, wherein the composition is a suspension.

6. The method of claim 1, wherein the taxane is paclitaxel, or a pharmaceutically acceptable salt thereof.

7. The method of claim 1, wherein the tumor is selected from the group consisting of sarcomas, carcinomas, and lymphomas, breast tumors, prostate tumors, head and neck tumors, glioblastomas, bladder tumors, pancreatic tumors, liver tumors, ovarian tumors, colorectal tumors, cutaneous, lymphoid, and gastrointestinal tumors.

8. The method of claim 7, wherein the tumor is selected from the group consisting of ovarian, bladder, breast, prostate, pulmonary, pancreatic, cutaneous, lymphoid, and gastrointestinal tumors.

9. The method of claim 1, wherein the taxane is docetaxel, or a pharmaceutically acceptable salt thereof.

10. The method of claim 9, wherein the tumor is selected from the group consisting of ovarian, bladder, breast, and prostate tumors.

11. The method of claim 1, wherein the taxane particles comprise at least 98% taxane.

12. The method of claim 11, wherein the taxane particles have an SSA of between about 18 m$^2$/g and about 50 m$^2$/g.

13. The method of claim 1, wherein the taxane is paclitaxel or a pharmaceutically acceptable salt thereof, and wherein the particles have a mean bulk density between about 0.050 g/cm$^3$ and about 0.12 g/cm$^3$.

14. The method of claim 1, wherein the taxane is paclitaxel or a pharmaceutically acceptable salt thereof, and wherein the paclitaxel particles have a SSA of between about 22 m$^2$/g and about 40 m$^2$/g.

15. The method of claim 1, wherein the taxane is docetaxel or a pharmaceutically acceptable salt thereof, and wherein the particles have a mean bulk density between about 0.050 g/cm$^3$ and about 0.12 g/cm$^3$.

16. The method of claim 1, wherein the taxane is docetaxel or a pharmaceutically acceptable salt thereof, and wherein the docetaxel particles have a SSA of between about 18 m$^2$/g and about 50 m$^2$/g.

17. The method of claim 16, wherein the docetaxel particles have a bulk density of between about 0.06 g/cm$^3$ and about 0.1 g/cm$^3$.

18. The method of claim 1, wherein the particles have a mean particle size number of between about 0.4 μm and about 1.2 μm.

19. The method of claim 5, wherein the suspension further comprises a polysorbate, wherein the polysorbate is present in the suspension at a concentration of between about 0.01% v/v and about 1.5% v/v.

20. The method of claim 5, wherein the taxane is present in the suspension at a concentration between about 1 mg/ml and about 40 mg/ml.

21. The method of claim 1 wherein the taxane particles are (i) uncoated; (ii) not embedded, contained, enclosed or encapsulated within a solid excipient; and (iii) not microspheres, liposomes, or microcapsules containing taxane and an excipient.

22. The method of claim 1, wherein the taxane particles are uncoated and the composition excludes polymers, proteins, polyethoxylated castor oil, and/or polyethylene glycol glycerides composed of mono-, di- and triglycerides and mono- and diesters of polyethylene glycol.

* * * * *